(12) United States Patent
Li et al.

(10) Patent No.: US 8,334,405 B2
(45) Date of Patent: Dec. 18, 2012

(54) CHIRAL THIOUREA COMPOUNDS AND PROCESS FOR ENANTIOSELECTIVE REDUCTION OF KETONES

(75) Inventors: Derun Li, Somerville, MA (US); John R. Falck, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 661 days.

(21) Appl. No.: 12/080,634

(22) Filed: Apr. 3, 2008

(65) Prior Publication Data
US 2009/0253919 A1 Oct. 8, 2009

(51) Int. Cl.
*C07C 335/00* (2006.01)

(52) U.S. Cl. .................. 564/31; 564/3; 564/17; 564/26

(58) Field of Classification Search .................. None
See application file for complete search history.

(56) References Cited

OTHER PUBLICATIONS

Pandey et al, Pharmacological Research Communications, 1981, 13(1), 65-74.*
Zu et al, J.Am.Chem.Soc., 2007, 129, 1036-1037.*
Fuerst et al, J.Am.Chem.Soc., 2005, 127, 8964-8965.*
Okino et al (J.Am.Chem.Soc., 2005, 127, 119-125).*
Burgess, K.; Jennings, L. D. J. Am. Chem. Soc. 1991, 113, 6129-6139.
Carter, M. B.; Schi0tt, B.; Gutiérrez, A.; Buchwald, S. L. J. Am. Chem. Soc. 1994, 116, 11667.
Corey, E. J.; Helal, C. J. Angew. Chem. Int. Ed. 1998, 37, 1986-2012.
Gamble, M. P.; Smith, A. R. C.; Wills, M. J. Org. Chem. 1998, 63, 6068-6071.
Huang, X.; Ortiz-Marciales, M.; Huang, K.; Stepanenko, V.; Merced, F. G.; Ayala, A. M.; Correa, W.; Jesu'S, M. D. Org. Lett. 2007, 9, 1793-1795.
J. Am. Chem. Soc. 2005, 127, 8964-8965.
J. Am. Chem. Soc. 2007, 129, 15872-15883.
Lutz, C.; Knochel, P. J. Org. Chem. 1997, 62, 7895-7898.
Node, M.; Nishide, K.; Shigeta, Y.; Shiraki, H.; Obata, K. J. Am. Chem. Soc. 2000, 122, 1927-1936.
Ohkuma, T.; Koizumi, M.; Yoshida, M.; Noyori, R. Org. Lett. 2000, 2, 1749-1751.
Sokeirik, Y. S.; Mori, H.; Omote, M.; Sato, K.; Tarui, A.; Kumadaki, I.; Ando, A. Org. Lett. 2007, 9, 1927-1929.
Tanaka, K.; Katsurada, M.; Ohno, F.; Shiga, Y.; Oda, M.; Miyagi, M.; Takehara, J.; Okano, K. J. Org. Chem. 2000, 65, 432.
Utsukihara, T.; Misumi, O.; Kato, N.; Kuroiwa, T.; Horiuchi C. A. Tetrahedron: Asymmetry 2006, 17, 1179-1185.
Wettergren, J.; Bogevig, A.; Portier,M.; Adolfssona, H. Adv. Synth. Catal. 2006, 348, 1277-1282.

* cited by examiner

*Primary Examiner* — Sudhakar Katakam
(74) *Attorney, Agent, or Firm* — Jackson Walker L.L.P.

(57) ABSTRACT

Chiral thioureas are effective catalysts for the borane reduction of prochiral ketones to optically active alcohols. A prochiral ketone may be reduced to an optically active alcohol in the presence of a substantially sub-stoichiometric amount of chiral thiourea. The asymmetric thiourea compound of the present invention may be produced according to a production method described herein.

18 Claims, 25 Drawing Sheets

PeakTable

Detector A Ch1 254nm

| Peak# | Ret. Time | Area | Height | Area % | Height % |
|---|---|---|---|---|---|
| 1 | 15.217 | 5195482 | 128317 | 49.887 | 55.218 |
| 2 | 19.684 | 5219004 | 104065 | 50.113 | 44.782 |
| Total | | 10414486 | 232382 | 100.000 | 100.000 |

PeakTable

Detector A Ch1 254nm

| Peak# | Ret. Time | Area | Height | Area % | Height % |
|---|---|---|---|---|---|
| 1 | 16.468 | 175384 | 4913 | 0.888 | 1.760 |
| 2 | 20.695 | 19582790 | 274225 | 99.112 | 98.240 |
| Total | | 19758174 | 279138 | 100.000 | 100.000 |

PeakTable

Detector A Ch1 254nm

| Peak# | Ret. Time | Area | Height | Area % | Height % |
|---|---|---|---|---|---|
| 1 | 14.257 | 3663280 | 96891 | 49.987 | 53.365 |
| 2 | 17.526 | 3665159 | 84671 | 50.013 | 46.635 |
| Total | | 7328440 | 181561 | 100.000 | 100.000 |

1 Det.A Ch1/254nm

PeakTable

Detector A Ch1 254nm

| Peak# | Ret. Time | Area | Height | Area % | Height % |
|---|---|---|---|---|---|
| 1 | 14.444 | 32400 | 1026 | 0.501 | 0.752 |
| 2 | 17.388 | 6438129 | 135380 | 99.499 | 99.248 |
| Total | | 6470530 | 136406 | 100.000 | 100.000 |

PeakTable

Detector A Ch1 254nm

| Peak# | Ret. Time | Area | Height | Area % | Height % |
|---|---|---|---|---|---|
| 1 | 21.035 | 2502206 | 42447 | 49.845 | 50.752 |
| 2 | 23.829 | 2517729 | 41190 | 50.155 | 49.248 |
| Total | | 5019935 | 83637 | 100.000 | 100.000 |

PeakTable

Detector A Ch1 254nm

| Peak# | Ret. Time | Area | Height | Area % | Height % |
|---|---|---|---|---|---|
| 1 | 21.883 | 15556 | 358 | 0.719 | 1.011 |
| 2 | 23.871 | 2147085 | 35083 | 99.281 | 98.989 |
| Total | | 2162641 | 35442 | 100.000 | 100.000 |

PeakTable

Detector A Ch1 254nm

| Peak# | Ret. Time | Area | Height | Area % | Height % |
|---|---|---|---|---|---|
| 1 | 14.441 | 5024407 | 173407 | 48.499 | 54.921 |
| 2 | 17.388 | 5335511 | 142332 | 51.501 | 45.079 |
| Total | | 10359918 | 315739 | 100.000 | 100.000 |

PeakTable

Detector A Ch1 254nm

| Peak# | Ret. Time | Area | Height | Area % | Height % |
|---|---|---|---|---|---|
| 1 | 14.059 | 17841692 | 469701 | 98.027 | 97.510 |
| 2 | 17.656 | 359153 | 11992 | 1.973 | 2.490 |
| Total | | 18200845 | 481694 | 100.000 | 100.000 |

PeakTable

Detector A Ch1 254nm

| Peak# | Ret. Time | Area | Height | Area % | Height % |
|---|---|---|---|---|---|
| 1 | 18.757 | 58901696 | 587336 | 48.893 | 61.400 |
| 2 | 22.225 | 61568771 | 369231 | 51.107 | 38.600 |
| Total | | 120470468 | 956567 | 100.000 | 100.000 |

PeakTable

Detector A Ch1 254nm

| Peak# | Ret. Time | Area | Height | Area % | Height % |
|---|---|---|---|---|---|
| 1 | 18.448 | 279574 | 5313 | 1.230 | 2.135 |
| 2 | 20.399 | 22451339 | 243501 | 98.770 | 97.865 |
| Total | | 22730914 | 248814 | 100.000 | 100.000 |

PeakTable

Detector A Ch1 254nm

| Peak# | Ret. Time | Area | Height | Area % | Height % |
|---|---|---|---|---|---|
| 1 | 37.636 | 5012167 | 41185 | 50.687 | 54.167 |
| 2 | 42.672 | 4876271 | 34848 | 49.313 | 45.833 |
| Total | | 9888439 | 76033 | 100.000 | 100.000 |

1 Det.A Ch1/254nm

PeakTable

Detector A Ch1 254nm

| Peak# | Ret. Time | Area | Height | Area % | Height % |
|---|---|---|---|---|---|
| 1 | 36.457 | 21935304 | 152759 | 99.530 | 99.336 |
| 2 | 43.071 | 103686 | 1021 | 0.470 | 0.664 |
| Total | | 22038989 | 153781 | 100.000 | 100.000 |

PeakTable

Detector A Ch1 254nm

| Peak# | Ret. Time | Area | Height | Area % | Height % |
|---|---|---|---|---|---|
| 1 | 22.632 | 3112787 | 44596 | 49.903 | 54.482 |
| 2 | 25.512 | 3124831 | 37258 | 50.097 | 45.518 |
| Total | | 6237618 | 81854 | 100.000 | 100.000 |

PeakTable

Detector A Ch1 254nm

| Peak# | Ret. Time | Area | Height | Area % | Height % |
|---|---|---|---|---|---|
| 1 | 22.184 | 12950920 | 155583 | 99.494 | 99.328 |
| 2 | 25.872 | 65834 | 1052 | 0.506 | 0.672 |
| Total | | 13016754 | 156636 | 100.000 | 100.000 |

PeakTable

Detector A Ch1 254nm

| Peak# | Ret. Time | Area | Height | Area % | Height % |
|---|---|---|---|---|---|
| 1 | 25.094 | 2478207 | 31209 | 50.075 | 53.949 |
| 2 | 28.683 | 2470749 | 26639 | 49.925 | 46.051 |
| Total | | 4948956 | 57848 | 100.000 | 100.000 |

1  Det.A Ch1/254nm

PeakTable

Detector A Ch1 254nm

| Peak# | Ret. Time | Area | Height | Area % | Height % |
|---|---|---|---|---|---|
| 1 | 24.568 | 10029031 | 110179 | 99.591 | 99.486 |
| 2 | 28.923 | 41200 | 569 | 0.409 | 0.514 |
| Total | | 10070230 | 110749 | 100.000 | 100.000 |

PeakTable

Detector A Ch1 254nm

| Peak# | Ret. Time | Area | Height | Area % | Height % |
|---|---|---|---|---|---|
| 1 | 16.397 | 4169825 | 97648 | 50.025 | 52.388 |
| 2 | 18.423 | 4165710 | 88747 | 49.975 | 47.612 |
| Total | | 8335535 | 186395 | 100.000 | 100.000 |

PeakTable

Detector A Ch1 254nm

| Peak# | Ret. Time | Area | Height | Area % | Height % |
|---|---|---|---|---|---|
| 1 | 16.241 | 7963948 | 166589 | 99.443 | 99.305 |
| 2 | 18.679 | 44593 | 1165 | 0.557 | 0.695 |
| Total | | 8008541 | 167754 | 100.000 | 100.000 |

PeakTable

Detector A Ch1 254nm

| Peak# | Ret. Time | Area | Height | Area % | Height % |
|---|---|---|---|---|---|
| 1 | 15.531 | 14775439 | 347688 | 48.862 | 62.245 |
| 2 | 19.756 | 15463959 | 210895 | 51.138 | 37.755 |
| Total | | 30239399 | 558583 | 100.000 | 100.000 |

PeakTable

Detector A Ch1 254nm

| Peak# | Ret. Time | Area | Height | Area % | Height % |
|---|---|---|---|---|---|
| 1 | 16.123 | 3230933 | 102963 | 98.773 | 98.918 |
| 2 | 21.225 | 40140 | 1126 | 1.227 | 1.082 |
| Total | | 3271073 | 104090 | 100.000 | 100.000 |

PeakTable

Detector A Ch1 254nm

| Peak# | Ret. Time | Area | Height | Area % | Height % |
|---|---|---|---|---|---|
| 1 | 26.223 | 2552584 | 59862 | 49.960 | 57.015 |
| 2 | 33.859 | 2556668 | 45131 | 50.040 | 42.985 |
| Total | | 5109252 | 104993 | 100.000 | 100.000 |

1  Det.A Ch1/254nm

PeakTable

Detector A Ch1 254nm

| Peak# | Ret. Time | Area | Height | Area % | Height % |
|---|---|---|---|---|---|
| 1 | 25.726 | 12702118 | 267391 | 99.085 | 99.166 |
| 2 | 33.771 | 117315 | 2250 | 0.915 | 0.834 |
| Total | | 12819433 | 269641 | 100.000 | 100.000 |

PeakTable

Detector A Ch1 254nm

| Peak# | Ret. Time | Area | Height | Area % | Height % |
|---|---|---|---|---|---|
| 1 | 30.092 | 8637146 | 146707 | 52.589 | 58.809 |
| 2 | 37.484 | 7786764 | 102755 | 47.411 | 41.191 |
| Total | | 16423910 | 249462 | 100.000 | 100.000 |

PeakTable

Detector A Ch1 254nm

| Peak# | Ret. Time | Area | Height | Area % | Height % |
|---|---|---|---|---|---|
| 1 | 30.044 | 9106451 | 153540 | 97.761 | 97.574 |
| 2 | 38.335 | 208539 | 3818 | 2.239 | 2.426 |
| Total | | 9314989 | 157357 | 100.000 | 100.000 |

PeakTable

Detector A Ch1 254nm

| Peak# | Ret. Time | Area | Height | Area % | Height % |
|---|---|---|---|---|---|
| 1 | 15.994 | 95021379 | 2317777 | 48.402 | 54.523 |
| 2 | 22.846 | 101294977 | 1933241 | 51.598 | 45.477 |
| Total | | 196316355 | 4251018 | 100.000 | 100.000 |

PeakTable

Detector A Ch1 254nm

| Peak# | Ret. Time | Area | Height | Area % | Height % |
|---|---|---|---|---|---|
| 1 | 16.029 | 1430847 | 41278 | 5.054 | 7.250 |
| 2 | 22.807 | 26881031 | 528072 | 94.946 | 92.750 |
| Total | | 28311878 | 569350 | 100.000 | 100.000 |

PeakTable

Detector A Ch1 254nm

| Peak# | Ret. Time | Area | Height | Area % | Height % |
|---|---|---|---|---|---|
| 1 | 13.011 | 2559620 | 80983 | 50.768 | 61.555 |
| 2 | 20.532 | 2482162 | 50580 | 49.232 | 38.445 |
| Total | | 5041781 | 131563 | 100.000 | 100.000 |

PeakTable

Detector A Ch1 254nm

| Peak# | Ret. Time | Area | Height | Area % | Height % |
|---|---|---|---|---|---|
| 1 | 13.020 | 382399 | 11539 | 6.915 | 9.937 |
| 2 | 20.556 | 5147705 | 104585 | 93.085 | 90.063 |
| Total | | 5530104 | 116125 | 100.000 | 100.000 |

| Peak# | Ret. Time | Area | Height | Area % |
|---|---|---|---|---|
| 1 | 12.271 | 23025141 | 486438 | 52.962 |
| 2 | 15.111 | 20449762 | 334456 | 47.038 |
| Total | | 43474904 | 820894 | 100.000 |

PeakTable

| Peak# | Ret. Time | Area | Height | Area % |
|---|---|---|---|---|
| 1 | 12.740 | 22007040 | 483626 | 98.860 |
| 2 | 16.036 | 253845 | 5611 | 1.140 |
| Total | | 22260885 | 489237 | 100.000 |

PeakTable

Detector A Ch1 254nm

| Peak# | Ret. Time | Area | Height | Area % | Height % |
|---|---|---|---|---|---|
| 1 | 11.109 | 9759084 | 346012 | 43.554 | 49.022 |
| 2 | 14.705 | 12647542 | 359811 | 56.446 | 50.978 |
| Total | | 22406626 | 705822 | 100.000 | 100.000 |

PeakTable

Detector A Ch1 254nm

| Peak# | Ret. Time | Area | Height | Area % |
|---|---|---|---|---|
| 1 | 11.165 | 1103157 | 38484 | 10.580 |
| 2 | 15.525 | 9323368 | 250740 | 89.420 |
| Total | | 10426526 | 289224 | 100.000 |

1 Det.A Ch1/254nm

PeakTable

Detector A Ch1 254nm

| Peak# | Ret. Time | Area | Height | Area % |
|---|---|---|---|---|
| 1 | 31.921 | 46434821 | 713230 | 95.803 |
| 2 | 35.051 | 2034201 | 34307 | 4.197 |
| Total | | 48469022 | 747537 | 100.000 |

CHIRAL THIOUREA COMPOUNDS AND PROCESS FOR ENANTIOSELECTIVE REDUCTION OF KETONES

The present invention used, in parts, finds from NIH Grant No. GM31278. The United States may have certain rights in the invention.

BACKGROUND

The present invention relates to thiourea compounds useful as catalysts for asymmetric reactions. Moreover, the present invention pertains to methods of reacting a prochiral ketone catalyzed by a chiral thiourea catalyst in the presence of a borane.

Chirality continues to play an important role in the development of new pharmaceutical intermediates. Among the numerous techniques available today to industrial chemists, asymmetric synthesis has been used widely to obtain enantioenriched compounds. In many industrial processes, asymmetric catalysis is becoming the preferred approach because of its lower environmental impact and higher potential productivity. The asymmetric reduction of prochiral ketones to enantioenriched secondary alcohols is a prominent example of such a transformation in organic synthesis While an array of options is available, current demands for more economic and environmentally friendly protocols, especially metal free reagents, have introduced new challenges. One of the most widely applied, despite its sensitivity to air and moisture, of this new generation of catalytic asymmetric reducing systems is the Corey-Bakshi-Shibata ("CBS") oxaborolidine.

In addition to their high costs and air and moisture sensitivity, B—H oxazaborolidines often contain impurities which diminish their effectiveness.

SUMMARY

Chiral thiourea compounds are catalytic for the reduction of a prochiral ketone to an optically active alcohol, meaning that a prochiral ketone may be reduced to an optically active alcohol in the presence of a substantially sub-stoichiometric amount of chiral thiourea.

Accordingly, the present invention pertains to the following:

(1) A chiral thiourea represented by the formula (I):

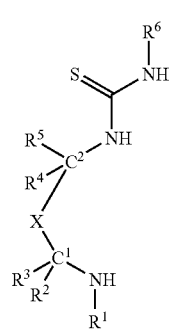

(I)

in which:

X is a bond connecting $C^1$ and $C^2$ and contains "no additional atom(s)," C, C—C, O, N, or S;

$C^1$ and $C^2$ are each independently an asymmetric center, wherein at least one of $C^1$ and $C^2$ is an asymmetric center;

$R^1$ is a substituted or un-substituted lower alkyl group, excluding isobutyl, a substituted or un-substituted aralkyl group, a substituted or un-substituted aryl group, or a substituted or un-substituted heteroaryl group;

$R^2$ and $R^4$ are the same or different and each independently is H, a substituted or un-substituted lower alkyl group, a substituted or un-substituted aralkyl group, a substituted or un-substituted aryl group, or $R^2$ and $R^4$ optionally form, together with the asymmetric carbons they are respectively bonded to, a substituted or un-substituted homocyclic ring or a substituted or un-substituted heterocycle;

$R^3$ and $R^5$ are the same or different and each independently is H, a substituted or un-substituted lower alkyl group;

$R^6$ is a substituted or un-substituted lower alkyl group, a substituted or un-substituted aralkyl group, a substituted or un-substituted aryl group, or a substituted or un-substituted heteroaryl group, or is:

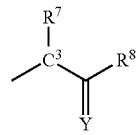

wherein $C^3$ is a chiral carbon atom, Y is S or O, and $R^7$ and $R^8$ independently are an alkyl, alkenyl, alkynyl, acyl, thioacyl, alkylthio, imine, amide, phosphoryl, phosphonate, phosphine, carbonyl, carboxyl, carboxamide, anhydride, silyl, thioakyl, alkylsulfonyl, arylsulfonyl, ketones, aldehyde, ester, heteroalkyl, amidine, acetal, ketal, aryl, heteroaryl, aziridine, carbamate, imide, oxime, sulfonamide, thioamide, thiocarbamate, urea, thiourea.

In certain embodiments, $R^8$ represents an amino group, such as a primary or secondary amino group. For example, $R^8$ can be represented by:

wherein $R^9$ and $R^{10}$ each independently are H, a lower alkyl, an aralkyl, such as N,N-dimethylamino, N-methyl-N-benzylamino or the like, or $R^9$ and $R^{10}$ taken together with the N atom to which they are attached complete a heterocycle having from 4 to 8 atoms in the ring structure, such as piperidinyl, pyrrolidinyl, and the like.

In compound (I), $R^2$, $R^3$, $R^4$, $R^5$ are in a combination which maintains the chirality of the compound.

In additional embodiments, in the asymmetric compound (I), $R^2$ and $R^4$ may form, together with asymmetric carbons they are respectively bonded to, a cyclopropane, a cyclobutane, a cyclopentane, a cyclohexane, or a salt thereof.

In additional embodiments, the chiral thiourea compound is represented by formula (II) below, wherein $R^2$ and $R^4$, together with the asymmetric carbons they are respectively bonded to, form a cyclohexane, and $R^3$ and $R^5$ are each H, and $R^1$ and $R^6$ are defined as above.

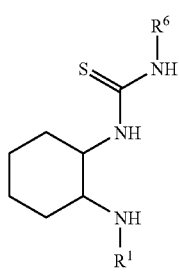

(II)

In additional embodiment, the chiral thiourea compound is represented by formula (III) below, wherein an axial chirality is formed by binaphthyl atropisomers and $R^1$ and $R^6$ are defined as above.

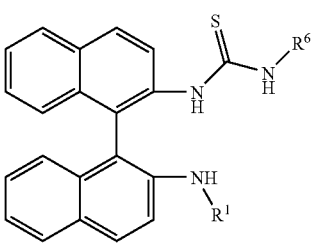

(III)

The current invention also pertains to a method to enantioselectively reduce a prochiral ketone, as shown in FIG. 1. The prochiral ketone, represented by $R^{11}COR^{12}$, formula (IV), is reduced to a optically active alcohol, represented by $R^{11}CHOHR^{12}$, formula (VI). The steps in the method include reacting the prochiral ketone $R^{11}COR^{12}$ (IV) with borane (V) in the presence of a catalytically effective amount of catalyst. The catalyst is a chiral thiourea of formula (I) in a solvent. Borane (V) can be $BH_3.THF$, $BH_3.Me_2S$, $BH_3.1,4$-thioxane, $BH_3$.diethylaniline, catecholborane or similar compounds. Catecholborane is preferred. The prochiral ketone, represented by $R^{11}COR^{12}$, formula (IV), is a ketone in which $R^{11}$ and $R^{12}$ are non-identical, so that the secondary alcohol reduction product, $R^{11}CHOHR^{12}$, formula (VI), has a chiral center at the alcohol carbon. The prochiral ketone may be any prochiral ketone in which $R^{11}$ and $R^{12}$ are inert to borane. That is, $R^{11}$ and $R^{12}$ may independently be any organic radicals, such as alkyl, aryl, or aralkyl. The term "alkyl" is used here in its broadest sense as meaning non-aromatic hydrocarbyl, and includes alkenyl. The term "aryl" means aromatic hydrocarbyl, and includes phenyl and naphthyl. $R^{11}$ and $R^{12}$ may be taken together to form a ring system so that $R^{11}COR^{12}$ is cyclic, such as tetralone. $R^{11}$ and $R^{12}$ may independently be substituted with any borane-inert substituents, such as alkyl, alkoxy, or halo.

The extent of enantioselectivity of the reduction process of the method will depend to some extent of the relative sizes of $R^{11}$ and $R^{12}$. A greater difference in size creates a greater enantiomeric excess, other conditions being equal.

Unlike known Corey-Bakshi-Shibata ("CBS") oxaborolidine catalysts, catalysts of the present invention are mostly air and moisture stable, making these catalyst easy to handle in the laboratories.

DETAILED DESCRIPTION OF THE PREFERRED EMBODIMENTS

Definitions

Figure 1:
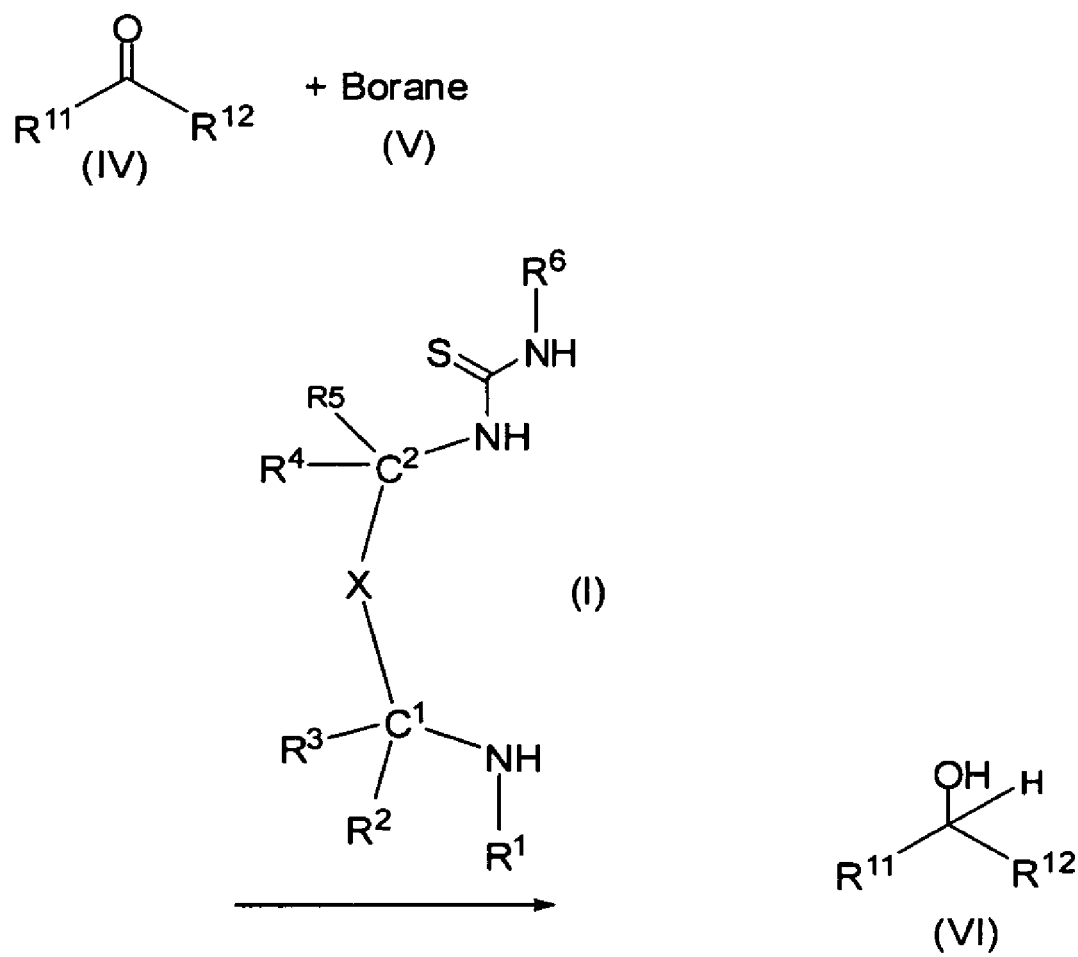
FIG. 1 shows a schematic of a general method to enantioselectively reduce a prochiral ketone.

The following definitions pertain to the terms as used herein, and are those commonly known in the art, unless the context otherwise requires.

"Alkyl" means a branched, unbranched, or cyclic saturated hydrocarbon group. Examples are methyl, ethyl, 2-propyl, 1-butyl, neopentyl(2,2-dimethyl-1-propyl), hexyl, cyclohexyl, cyclopentylmethyl, tert-octyl(1,1,3,3-tertramethyl-1-butyl), and the like.

"Lower alkyl" means a branched, unbranched, or cyclic saturated hydrocarbon group containing from 1 to 12 carbon atoms. Examples are methyl, ethyl, 2-propyl, 1-butyl, isobutyl, sec-butyl, tert-butyl, pentyl, isopentyl, neopentyl(2,2-dimethyl-1-propyl), hexyl, cyclohexyl, heptyl, octyl, nonyl, decyl, undecyl, dodecyl, cyclopentylmethyl, tert-octyl(1,1,3,3-tertramethyl-1-butyl), and the like.

"Halogen atom" means fluorine atom, chlorine atom, bromine atom or iodine atom.

"Lower alkoxy group" means an alkoxy group wherein the alkyl moiety is the "lower alkyl" defined above, and, for example, methoxy, ethoxy, propoxy, isopropoxy, butoxy, isobutoxy, sec-butoxy, tert-butoxy, pentoxy, isopentoxy, neopentoxy, hexyloxy, heptyloxy, octyloxy, nonyloxy, decyloxy, undecyloxy, dodecyloxy, and the like.

"Mono-lower alkylamino group" means a mono-alkylamino group wherein the alkyl moiety is the "lower alkyl" defined above, and for example, N-methylamino, N-ethylamino, N-propylamino, N-isopropylamino, N-butylamino, N-isobutylamino, N-sec-butylamino, N-tert-butylamino and the like.

"Di-lower alkylamino group" means a di-alkylamino group wherein the alkyl moieties are the same or different and each is the "lower alkyl group" defined above, and, for example, N,N-dimethylamino, N,N-diethylamino, N,N-dipropylamino, N,N-diisopropylamino, N,N-dibutylamino, N,N-diisobutylamino, N,N-di-sec-butylamino, N,N-di-tert-butylamino, N,N-dihexylamino, N,N-dicyclohexylamino, N-methyl-N-ethylamino, N-methyl-N-propylamino, N-methyl-N-isopropylamino, N-methyl-N-butylamino, N-methyl-N-isobutylamino, N-methyl-N-sec-butylamino, N-methyl-N-tert-butylamino and the like.

"Aryl" means either phenyl or 1- or 2-naphthyl, biphenyl, binaphthyl and the like. Each optionally has substituent(s) at substitutable position(s), such as a lower alkyl group (as defined above), a lower alkoxy group (as defined above), a mono-lower alkylamino group (as defined above), a di-lower alkylamino group (exemplified by those defined above), a substituted or unsubstituted piperidinyl, a substituted or unsubstituted pyrrolidinyl, a halogen atom (as defined above), a haloalkyl group, which is a lower alkyl group substituted by one or more halogen atoms, such as trifuloromethyl, a nitro group, an ester, and the like. The number of the substituents is not particularly limited, but is preferably 1 to 3. When it is 2 or more, the substituents may be the same or different.

"Aralkyl" means "lower alkyl group" defined above is substituted by the "aryl group" defined above at optional 1 to 10 position(s), and, for example, benzyl, 1- or 2-phenylethyl, 1-, 2-, or 3-phenylpropyl, 1- or 2-naphthylmethyl, benzhydryl, trityl and the like. The aralkyl group optionally has substituent(s) at substitutable position(s), including the same substituents mentioned above for the "aryl group." The number of the substituents is not particularly limited, but is preferably 1 to 3. When it is 2 or more, the substituents may be the same or different.

The "heteroaryl group" mentioned with regard to the "substituted or un-substituted heteroary group" for $R^1$ and $R^6$, for example, can be a 5- to 10-membered aromatic heterocyclic group containing, besides carbon atoms, 1 to 3 hetero atoms selected from an oxygen atom, a sulfur atom and a nitrogen atom, and a fused heterocyclic group and the like. For example, 2- or 3-thienyl, 2- or 3-furyl, 1-, 2- or 3-pyrroyl, 2-, 3-, or 4-pyridyl and the like. The heteroaryl group optionally has substituent(s) at substitutable position(s), such as the substituents listed for the "aryl group" above. The number of the substituents is not particularly limited, but is preferably 1 to 3. When it is 2 or more, the substituents may be the same or different.

A "catalytically effective" amount of a material is that sub-stoichiometric amount which is sufficient to facilitate the conversion of a desired reactant to product(s).

"Enantiomeric excess", or "e.e.," is the excess of one of two enantiomers over the other, usually expressed as a percentage. A 90% e.e. reflects the presence of 95% of one enantiomer and 5% of the other in the material in question.

"Borane" is $BH_3.THF$, $BH_3.Me_2S$, $BH_3.1,4$-thioxane, $BH_3.$diethylaniline, catecholborane and the like. Catecholborane is preferred.

A "prochiral ketone," represented by $R^{11}COR^{12}$, or formula (IV) in FIG. 1, is a ketone in which $R^{11}$ and $R^{12}$ are non-identical, so that the secondary alcohol reduction product, $R^{11}CHOHR^{12}$, (formula (VI) in FIG. 1), has a chiral center at the alcohol carbon. The prochiral ketone, $R^{11}COR^{12}$ (IV), may be any prochiral ketone in which $R^{11}$ and $R^{12}$ are inert to borane. That is, $R^{11}$ and $R^{12}$ may independently be any organic radicals, such as alkyl, aryl, or aralkyl. The term "alkyl" is used here in its broadest sense as meaning non-aromatic hydrocarbyl, and includes alkenyl. The term "aryl" means aromatic hydrocarbyl, and includes phenyl and naphthyl. $R^{11}$ and $R^{12}$ may be taken together to form a ring system so that $R^{11}COR^{12}$ is cyclic, such as tetralone. $R^{11}$ and $R^{12}$ may independently be substituted with any borane-inert substituents, such as alkyl, alkoxy, or halo.

The present invention pertains to a chiral thiourea represented by the formula (I):

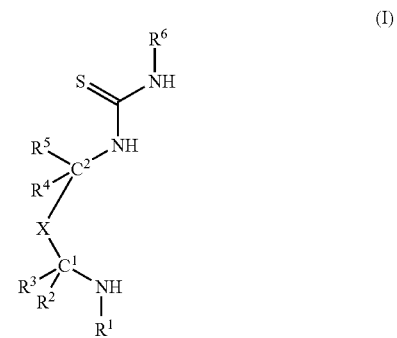

(I)

wherein:

X is a bond connecting $C^1$ and $C^2$ and contains "no additional atom(s)," C, C—C, O, N, or S;

$C^1$ and $C^2$ are each carbon and are independently an asymmetric center or a non-asymmetric center, wherein at least one of $C^1$ and $C^2$ is an asymmetric center;

$R^1$ is a substituted or un-substituted lower alkyl group, a substituted or un-substituted aralkyl group, a substituted or un-substituted aryl group, or a substituted or un-substituted heteroaryl group, wherein $R^1$ is not isobutyl;

$R^2$ and $R^4$ are the same or different and each independently is H, a substituted or un-substituted lower alkyl group, a substituted or un-substituted aralkyl group, a substituted or un-substituted aryl group, or $R^2$ and $R^4$ optionally form, together with the asymmetric carbons they are respectively bonded to, a substituted or un-substituted homocyclic ring or a substituted or un-substituted heterocycle;

$R^3$ and $R^5$ are the same or different and each independently is H, a substituted or un-substituted lower alkyl group;

$R^6$ is a substituted or un-substituted lower alkyl group, a substituted or un-substituted aralkyl group, a substituted or un-substituted aryl group, or a substituted or un-substituted heteroaryl group, or is:

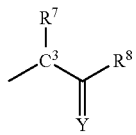

wherein $C^3$ is a chiral carbon atom, Y is S or O, and $R^7$ and $R^8$ independently are an alkyl, alkenyl, alkynyl, acyl, thioacyl, alkylthio, imine, amide, phosphoryl, phosphonate, phosphine, carbonyl, carboxyl, carboxamide, anhydride, silyl, thioakyl, alkylsulfonyl, arylsulfonyl, ketones, aldehyde, ester, heteroalkyl, amidine, acetal, ketal, aryl, heteroaryl, aziridine, carbamate, imide, oxime, sulfonamide, thioamide, thiocarbamate, urea, or thiourea.

In certain embodiments, $R^8$ represents an amino group, such as a primary or secondary amino group. For example, $R^8$ can be:

wherein $R^9$ and $R^{10}$ are the same or different and each independently is H, a lower alkyl, an aralkyl, or $R^9$ and $R^{10}$ taken together with the N atom to which they are attached complete a heterocycle having from 4 to 8 atoms in the ring structure. The aralkyl can be N,N-dimethylamino or N-methyl-N-benzylamino, and the heterocycle can be piperidinyl or pyrrolidinyl.

In compound (I), $R^2$, $R^3$, $R^4$, $R^5$ are in a combination which maintains the chirality of the compound.

In additional embodiments, in the asymmetric compound (I), $R^2$ and $R^4$ may form, together with asymmetric carbons they are respectively bonded to, a cyclopropane, a cyclobutane, a cyclopentane, a cyclohexane, or a salt thereof.

In additional embodiments, the chiral thiourea compound is represented by formula (II) below, wherein $R^2$ and $R^4$, together with the asymmetric carbons they are respectively bonded to, form a cyclohexane, and $R^3$ and $R^5$ are each H, and $R^1$ and $R^6$ are defined as above.

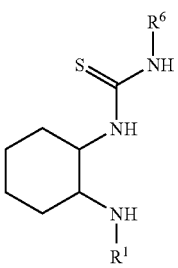

In additional embodiment, the chiral thiourea compound is represented by formula (III) below, wherein an axial chirality is formed by binaphthyl atropisomers and $R^1$ and $R^6$ are defined as above.

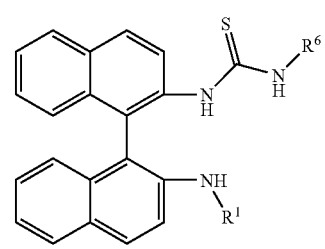

The current invention also pertains to a method to enantioselectively reduce a prochiral ketone, as shown in FIG. 1. The prochiral ketone, represented by $R^{11}COR^{12}$, formula (IV), is reduced to a optically active alcohol, represented by $R^{11}CHOHR^{12}$, formula (VI). The steps in the method include reacting the prochiral ketone $R^{11}COR^{12}$ (IV) with borane (V) in the presence of a catalytically effective amount of catalyst. The catalyst is a chiral thiourea of formula (I) in a solvent. Borane (V) can be $BH_3.THF$, $BH_3.Me_2S$, $BH_3.1,4$-thioxane, $BH_3.$diethylaniline, catecholborane or similar compounds. Catecholborane is preferred. The prochiral ketone, represented by $R^{11}COR^{12}$, formula (IV), is a ketone in which $R^{11}$ and $R^{12}$ are non-identical, so that the secondary alcohol reduction product, $R^{11}CHOHR^{12}$, formula (VI), has a chiral center at the alcohol carbon. The prochiral ketone may be any prochiral ketone in which $R^{11}$ and $R^{12}$ are inert to borane. That is, $R^{11}$ and $R^{12}$ may independently be any organic radicals, such as alkyl, aryl, or aralkyl. The term "alkyl" is used here in its broadest sense as meaning non-aromatic hydrocarbyl, and includes alkenyl. The term "aryl" means aromatic hydrocarbyl, and includes phenyl and naphthyl. $R^{11}$ and $R^{12}$ may be taken together to form a ring system so that $R^{11}COR^{12}$ is cyclic, such as tetralone. $R^{11}$ and $R^{12}$ may independently be substituted with any borane-inert substituents, such as alkyl, alkoxy, or halo.

The extent of enantioselectivity of the reduction process of the method will depend to some extent of the relative sizes of $R^{11}$ and $R^{12}$. A greater difference in size creates a greater enantiomeric excess, other conditions being equal.

The Preparation of the Catalyst

The preparations of the catalysts may be by techniques generally known to the art for the preparation of already-known thioureas, such as by the techniques disclosed in the references, or by the techniques discussed below.

Figure 2:
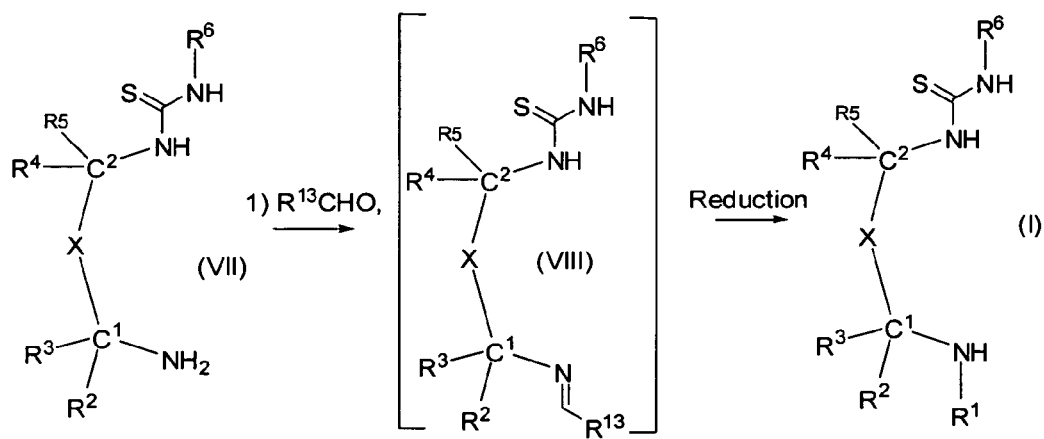
FIG. 2 shows a reaction scheme of one possible way of producing an asymmetric thiourea compound (I).

The asymmetric thiourea compound (I) of the present invention may be produced according to, but, not limited to, Production Method 1 shown by the reaction scheme in FIG. 2.

In this reaction scheme, each symbol is defined as above, and $R^{13}CHO$ is the corresponding aldehyde which could be transferred to $R^1$ group. In other words, asymmetric thiourea compound (I) may be synthesized by reacting a compound represented by formula (VII) (hereinafter to be also referred to as compound (VII)), with an aldehyde $R^{13}CHO$ to form intermediate an imine (VIII) in a solvent, followed by reduction by a reducing reagent in one pot.

In the first step of Production Method 1, the order of addition of compound (VII) and $R^{13}CHO$ is not particularly limited, and they may be added to a solvent simultaneously or successively. The amount of $R^{13}CHO$ to be used in the first step of Production Method 1 is preferably 0.5 mol to 5 mol, more preferably 0.9 mol to 1.5 mol, per 1 mol of compound (VII). As the solvent to be used in the first step of Production Method 1, any can be used as along as it does not inhibit the reaction. Methanol is preferred.

The reaction temperature in the first step of Production Method 1 is generally −78° C. to 100° C., and more preferably 0° C. to 40° C. While the reaction time varies depending on the reagent to be used and reaction temperature in the first step of Production Method 1, it is generally 1 hour to 10 hours. The reducing reagent which was used in the second step of Production Method 1 can be sodium borohydride ($NaBH_4$), sodium cyanoborohydride ($NaBH_3CN$), and the like. $NaBH_4$ is preferred.

The asymmetric thiourea compound (I) produced according to Production Method 1 can be isolated and purified according to a conventional method. For example, asymmetric thiourea compound (I) could be isolated by pouring a reaction mixture to saturated ammonium chloride aqueous solution, added ammonium hydroxide, extracted with organic solvent, e.g. dichloromethane, and concentrating the organic layer under reduced pressure. After isolation, the obtained product is purified, for example, by, but not limited to, silica gel column chromatography, or recrystallization.

The compound (VII), which is a starting material in Production Method 1, can be produced according to a known method (e.g., a method described in *J. Am. Chem. Soc.* 2005, 127, 8964-8965). For example, compound (VII) can be represented by formula (VIIa) shown below, which is preferable:

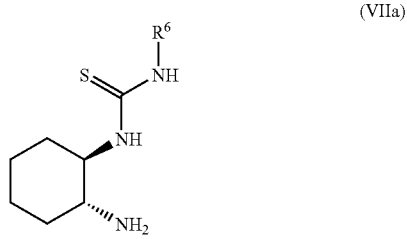

(VIIa)

In formula (VIIa), each symbol is as defined above, and can be produced according to the method described in *J. Am. Chem. Soc.* 2005, 127, 8964-8965, from the corresponding chiral diamine and the corresponding isothiocyanate, $R^6$—NCS. The isocyanate, $R^6$—NCS, which is one of the starting materials in the preparation of compound (VIIa), can be synthesized from an amine represented by $R^6$—$NH_2$, wherein $R^6$ is as defined above, according to a known method (*J. Am. Chem. Soc.* 2007, 129, 15872-15883), or a commercially available product can also be used.

The Reduction Method

Figure 3:
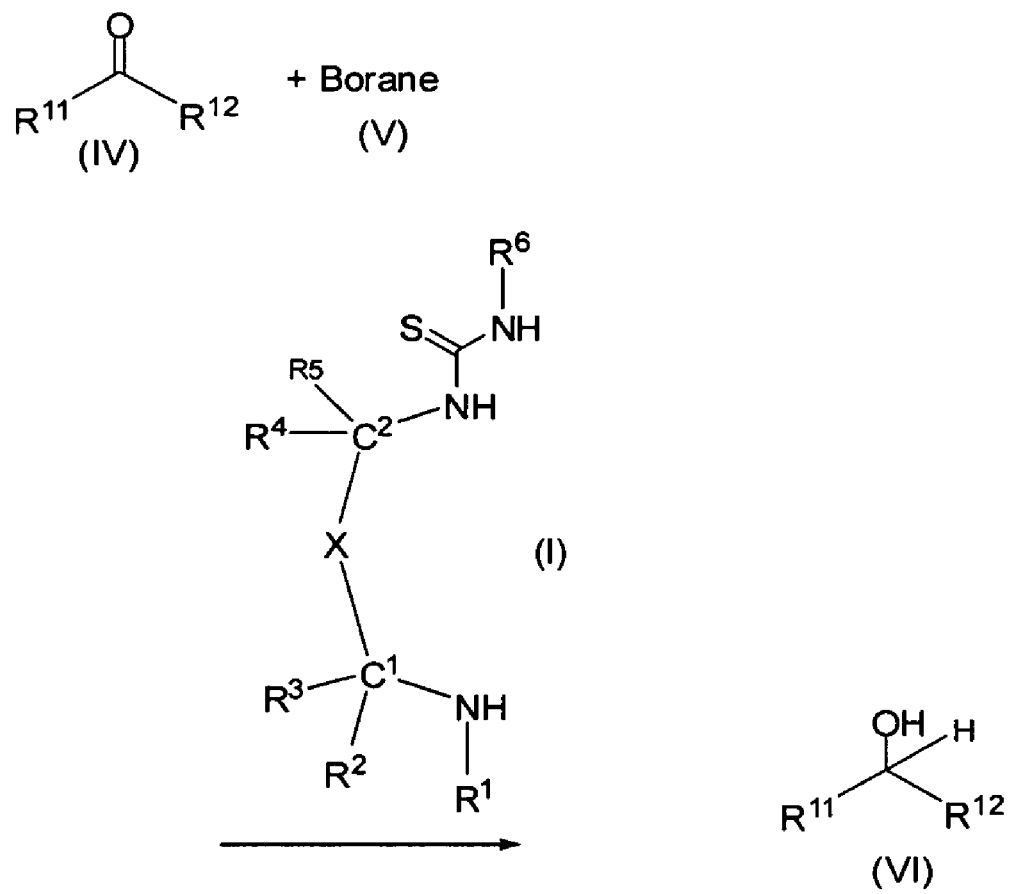
FIG. 3 shows a general scheme for reacting a prochiral ketone with borane in the presence of a catalytically effective amount of a chiral thiourea catalyst, to give an optically active alcohol.

The reduction method of the present invention is shown by the reaction scheme in FIG. 3, in which each symbol is defined as above.

The reduction method of the invention comprises reacting a prochiral ketone, represented by $R^{11}COR^{12}$ (IV), with borane (V) in the presence of a catalytically effective amount of catalyst which is a chiral thiourea (I), to give an optically active alcohol, represented by $R^{11}CHOHR^{12}$ (VI), in a solvent. In the reduction method, "borane (V)" can be $BH_3$.THF, $BH_3$.$Me_2S$, $BH_3$.1,4-thioxane, $BH_3$.diethylaniline, catecholborane and the like. Catecholborane is preferred.

In the reduction method, a "prochiral ketone", represented by $R^{11}COR^{12}$, formula (IV), is a ketone in which $R^{11}$ and $R^{12}$ are non-identical, so that the secondary alcohol reduction product, $R^{11}CHOHR^{12}$, (formula (VI)), has a chiral center at the alcohol carbon. The prochiral ketone, $R^{11}COR^{12}$ (IV), may be any prochiral ketone in which $R^{11}$ and $R^{12}$ are inert to borane. That is, $R^{11}$ and $R^{12}$ may independently be any organic radicals, such as alkyl, aryl, or aralkyl. The term "alkyl" is used here in its broadest sense as meaning non-aromatic hydrocarbyl, and includes alkenyl. The term "aryl" means aromatic hydrocarbyl, and includes phenyl and naphthyl, and they may be taken together to form a ring system so that $R^{11}COR^{12}$ is cyclic (such as tetralone). $R^{11}$ and $R^{12}$ may independently be substituted with any borane-inert substituents (such as alkyl, alkoxy, or halo). The extent of enantioselectivity of the reduction process of the invention will depend to some extent of the relative sizes of $R^{11}$ and $R^{12}$, a greater difference in size implying a greater enantiomeric excess, other conditions being equal.

The reduction method takes place in a suitable solvent, such as any solvent capable of sufficient dissolution of the catalyst and ketone, that is inert to borane, and does not inhibit the reaction. Suitable solvents are aprotic, non-basic solvents such as aromatic hydrocarbons (such as benzene or toluene), ethers (such as tetrahydrofuran, tetrahydropyran, or diethyl ether), aliphatic hydrocarbons and halogenated hydrocarbons. A preferred solvent is toluene. When a mixed solvent is used, they may be mixed at any ratio.

Typically, the catalyst and the prochiral ketone are dissolved in a suitable solvent, e.g. toluene, with or without the presence of a 4 Å molecular sieve, that should be freshly dried by flame under vacuum for 30 min and cooled under argon, at a temperature between −78° C. and 0° C., and preferably at about −46° C., and a solution of borane (catecholborane is preferred) added. Alternatively, the catalyst is dissolved in a solution of borane in a suitable solvent, with or without the presence of a 4 Å molecular sieve, that should be freshly dried by flame under vacuum for 30 min and cooled under argon, at a temperature between −78° C. and 0° C., and preferably at about −46° C., and the prochiral ketone in the same or another suitable solvent, or without solvent, being added. The order of the addition of prochiral ketone, $R^{11}COR^{12}$ (IV), borane (V) and chiral thiourea (I) is not limited.

The chiral thiourea catalyst (I) is employed in a catalytically effective amount, as defined previously. For a material to be considered a catalyst, a catalytically effective amount will be substantially sub-stoichiometric with respect to the reactant prochiral ketone, that is, it will be less than 0.5, preferably less than 0.25, more preferably no greater than 0.1 moles/mole of prochiral ketone. Yet lower amounts of catalyst, such as 0.01 to 0.05 moles/mole of prochiral ketone, may be employed and are functional. However, too little catalyst may (as with the presence of excessive borane) lead to uncatalyzed (and hence non-enantioselective) reduction of the prochiral ketone, lowering the e.e. of the product alcohol.

The amount of borane (V) to be used in the production method of the present invention is preferably 1 mol to 10 mol, more preferably 1.2 mol to 3 mol, per 1 mol of prochiral ketone. If desired, additional borane and prochiral ketone may be added to the reaction mixture and allowed to react further before the hydrolysis step, and this borane-prochiral ketone addition and reaction may be performed more than once before the final reaction mixture is hydrolyzed. This technique effectively decreases the catalyst/prochiral ketone ratio, in a fashion which still provides for adequate enantioselectivity of the reduction process.

The reaction time varies depending on the reagent to be used and reaction temperature, although it is generally 0.1 hours to 48 hours. The reaction produces a mixture containing the alkoxyborate. When the reaction is over, the reaction mixture may be quenched with alcohol, preferably methanol, and then treated with base, preferably 3 N NaOH aqueous solution, to generate the optical active alcohol product, $R^{11}CHOHR^{12}$. The product may be isolated by any conventional means, typically extraction with organic solvents, evaporation of the solvent and purified by conventional means such as chromatography, distillation, or other methods.

The chiral alcohols, $R^{11}CHOHR^{12}$, produced according to the production method of the present invention, are optically active, wherein the optical purity is not particularly limited. The chiral alcohols, $R^{11}CHOHR^{12}$, may be of interest as chiral reagents (such as 1-phenylethanol), or as intermediates in further chemical synthesis. For example, (S)-1-(3-(trifluoromethyl)phenyl)ethanol is the key intermediate for the synthesis of (S)-MA20565, a compound showing promise as a potent agricultural fungicide (Tanaka 2000).

EXAMPLES

The following examples illustrate the catalyst and reduction process of the invention, but should not be constructed to limit it.

Catalysts

Example 1

1-((1R,2R)-2-(benzylamino)cyclohexyl)-3-(3,5-bis(trifluoromethyl)phenyl)thiourea

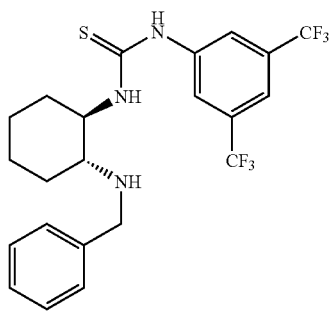

Figure 4:
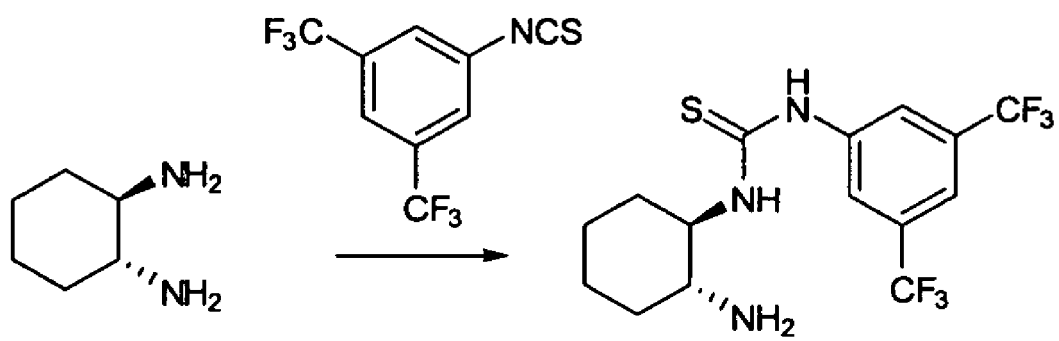
FIG. 4 shows a general scheme for the synthesis of 1-((1R,2R)-2-aminocyclohexyl)-3-(3,5-bis(trifluoromethyl)phenyl)thiourea.

As shown in FIG. 4, 3,5-Bis(trifluoromethyl)-phenyl isothiocyanate (1.3 mL, 7.1 mmol, 1.0 equiv) was added to a solution of (R,R)-cyclohexanediamine (970 mg, 8.51 mmol, 1.2 equiv) in anhydrous dichloromethane (20 mL) at rt. The resulting solution was stirred at room temperature ("rt") for 10 hours, then loaded onto a silica gel column and chromatographed (EtOAc/MeOH/NH$_4$OH, 200:5:1→100:20:1) to afford 1-((1R,2R)-2-aminocyclohexyl)-3-(3,5-bis(trifluoromethyl)phenyl)thiourea (2.0 g, 73% yield) as a yellow foam. R$_f$-0.31 (EtOAc/MeOH/NH$_4$OH, 100:5:1); $[\alpha]^{20}_D$=+76.9 (c 1.7, CHCl$_3$); $^1$H NMR (CDCl$_3$, 300 MHz) δ=8.01 (s, 2H), 7.55 (s, 1H), 1H), 3.37 (br s, 1H), 2.69-2.65 (m, 1H), 2.04 (m, 2H, NH$_2$), 1.98-1.91 (m, 2H), 1.80-1.65 (m, 2H), 1.40-1.20 (m, 4H); $^{13}$C NMR (CDCl$_3$, 75 MHz) δ=183.3, 142.0, 131.8 (q, J$_{CF}$=33.9 Hz), 128.8, 125.2, 122.9, 121.5, 117.9, 117.7, 63.4, 56.8, 35.1, 32.3, 24.7; HRMS (FAB, NBA) Calcd. for C$_{15}$H$_{18}$N$_3$SF$_6$ [MH$^+$] m/z 386.1125, found 386.1128.

Figure 5:
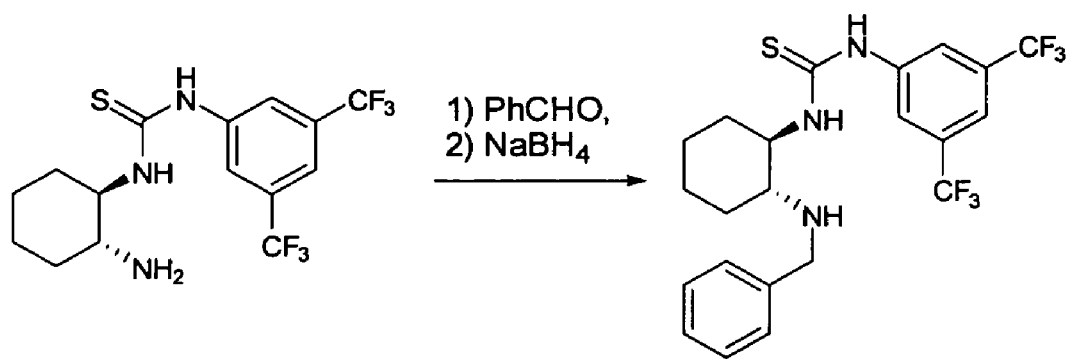
FIG. 5 shows a general scheme for the synthesis of 1-((1R,2R)-2-(benzylamino)cyclohexyl)-3-(3,5-bis(trifluoromethyl)phenyl)thiourea.

In the second step, as shown in FIG. 5, benzaldehyde (0.578 mL, 5.45 mmol, 1.05 equiv) was added to a solution of 1-((1R,2R)-2-aminocyclohexyl)-3-(3,5-bis(trifluoromethyl)phenyl)thiourea (2 g, 5.19 mmol, 1.0 equiv) in anhydrous MeOH (15 mL) under argon at rt. The resulting solution was stirred at rt for 4 hours, then cooled to 0° C. and NaBH$_4$ (211 mg, 5.71 mmol, 1.1 equiv) was added. The reaction mixture was stirred for 20 min and saturated NH$_4$Cl solution (50 mL) was added, followed by NH$_4$OH (2 mL). The resulting mixture was stirred for additional 20 min, then extracted with dichloromethane (100 mL×5), dried over Na$_2$SO$_4$, and evaporated to dryness. The residue was purified by flash chromatography on silica gel using Hexanes/EtOAc/MeOH/NH$_4$OH (400:100:5:1) to afford 1-((1R,2R)-2-(benzylamino)cyclohexyl)-3-(3,5-bis(trifluoromethyl)phenyl)thiourea (2.02 g, 82% yield) as pale yellow foam. The product was recrystallized from Hexanes/DCM in 75% yield as a white solid. mp 140° C.-141° C.; R$_f$-0.48 (DCM/MeOH, 9:1); $^1$H NMR (CDCl$_3$, 300 MHz) δ=7.69 (s, 2H), 7.48 (s, 1H), 7.29-7.20 (m, 5H), 6.59 (br s, 1H), AB (δ=3.97, 3.82, J$_{AB}$=12.3 Hz), 3.44 (br s, 1H), 2.49-2.42 (m, 1H), 2.18-2.00 (m, 2H), 1.90-1.75 (m, 2H), 1.40-1.20 (m, 4H); $^{13}$C NMR (CDCl$_3$, 75 MHz) δ=183.3, 141.8, 138.0, 131.5 (q, J$_{CF}$=30 Hz), 129.1, 128.6, 128.3, 128.1, 125.0, 122.4, 121.4, 117.1, 64.4, 62.5, 54.7, 33.2, 32.6, 24.9, 24.6; HRMS (FAB, NBA) Calcd. for C$_{22}$H$_{24}$N$_3$SF$_6$ [MH$^+$] m/z 476.1595, found 476.1598.

Figure 6:
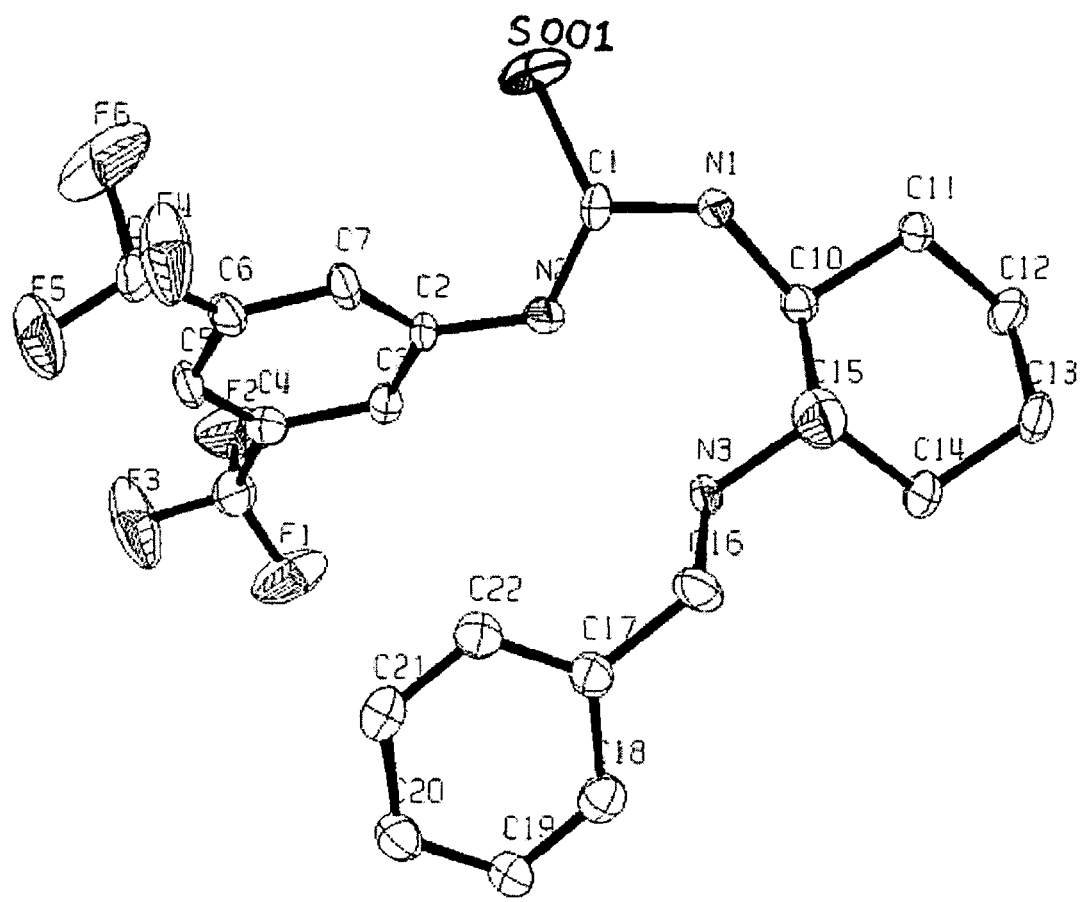
FIG. 6 shows a mirror image of 1-((1R,2R)-2-aminocyclohexyl)-3-(3,5-bis(trifluoromethyl)phenyl)thiourea.

FIG. 6 shows a mirror image of 1-((1R,2R)-2-aminocyclohexyl)-3-(3,5-bis(trifluoromethyl)phenyl)thiourea.

Example 2

(S)-2-(3-((1R,2R)-2-(benzylamino)cyclohexyl)thioureido)-N,3,3-trimethylbutanamide

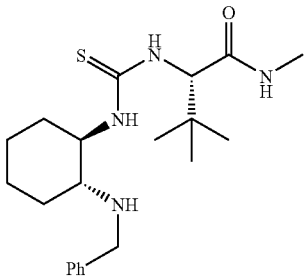

This compound was synthesized in the same manner as Example 1, except (S)-2-isothiocyanato-N,3,3-trimethylbutanamide was used instead of 3,5-bis(trifluoromethyl)-phenyl isothiocyanate. 54% yield. $[\alpha]^{20}_D$=54.9 (c 1.30, CHCl$_3$); $^1$H NMR (CDCl$_3$, 300 MHz) δ=7.99 (br s, 1H), 7.39-7.20 (m, 5H), 5.94 (br s, 2H), 4.77 (d, J=7.8 Hz, 1H), 3.79 (br s, 2H), 3.45 (br s, 1H), 2.78 (d, J=4.8 Hz, 3H), 2.40-2.35 (m, 1H), 2.10-1.95 (m, 1H), 1.95-1.80 (m, 2H), 1.75-1.65 (m, 2H), 1.27-1.12 (m, 4H), 1.00 (s, 9H); $^{13}$C NMR (CDCl$_3$, 75 MHz) δ=183.4, 171.5, 139.9, 128.7 (2C), 128.4 (2C), 127.3, 67.2, 61.1, 60.2, 51.7, 34.7, 32.8, 32.0, 27.0 (3C), 26.2, 24.8, 24.7; HRMS (ES) Calcd. for C$_{21}$H$_{35}$N$_4$OS [MH$^+$] m/z 391.2532, found 391.2529.

Example 3

(S)—N-benzyl-2-(3-((1R,2R)-2-(benzylamino)cyclohexyl)thioureido)-N,3,3-trimethylbutanamide

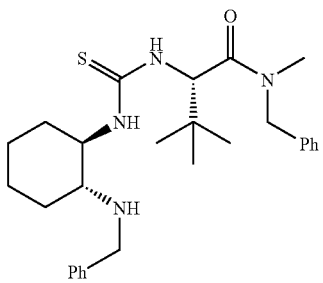

This compound was synthesized in the same manner as Example 1, except (S)—N-benzyl-2-isothiocyanato-N,3,3-trimethylbutanamide was used instead of 3,5-Bis(trifluoromethyl)-phenyl isothiocyanate. 50% yield. $[\alpha]^{20}_D$=24.5 (c 0.80, CHCl$_3$); $^1$H NMR (CDCl$_3$, 400 MHz) δ=7.92 (br s, 1H), 7.35-7.20 (m, 5H), 6.06 (d, J=1.2 Hz, 1H), 5.59 (d, J=9.2 Hz, 1H), 4.94 (d, J=14.4 Hz, 1H), 4.15 (d, J=14.4 Hz, 1H), AB (3.80, 3.76; J$_{AB}$=13.6 Hz), 3.46 (br s, 2H), 3.15 (s, 3H), 2.34-2.28 (m, 1H), 2.10-1.95 (m, 1H), 1.95-1.80 (m, 2H), 1.70-1.65 (m, 2H), 1.30-1.10 (m, 4H), 1.00 (s, 9H); $^{13}$C NMR (CDCl$_3$, 75 MHz) δ=183.1, 172.2, 140.1, 137.1, 128.7 (2C), 128.6 (2C), 128.6 (2C), 128.4 (4C), 127.6, 127.2, 61.4, 61.1, 60.2, 51.7, 51.4, 36.3, 36.2, 32.7, 31.9, 26.9 (3C), 24.8, 24.6; HRMS (FAB, NBA) Calcd. for C$_{28}$H$_{41}$N$_4$OS [MH$^+$] m/z 481.3001, found 481.2998.

Example 4

(S)-2-(3-((1R,2R)-2-(benzylamino)cyclohexyl)thioureido)-N—((R)-1-(dimethylamino)-3-methyl-1-oxobutan-2-yl)-3,3-dimethylbutanamide

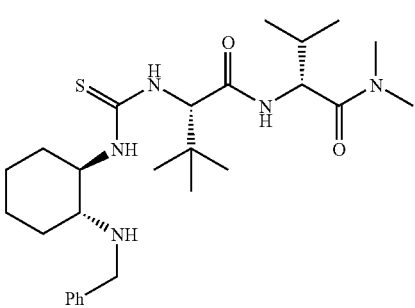

This compound was synthesized in the same manner as Example 1, except (S)—N—((R)-1-(dimethylamino)-3-methyl-1-oxobutan-2-yl)-2-isothiocyanato-3,3-dimethylbutanamide was used instead of 3,5-bis(trifluoromethyl)-phenyl isothiocyanate. 50% yield. $[\alpha]^{20}_D$=32.9 (c 2.05, CHCl$_3$); $^1$H NMR (CDCl$_3$, 300 MHz) δ=7.99 (br s, 1H), 7.29-7.18 (m, 5H), 6.75 (d, J=7.8 Hz, 1H), 6.20 (d, J=5.4 Hz, 1H), 4.78 (d, J=5.1 Hz, 1H), 4.76 (d, J=5.4 Hz, 1H), 3.77 (br s, 2H), 3.48 (br s, 1H), 3.03 (s, 3H), 2.91 (s, 3H), 2.40-2.35 (m, 1H), 2.10-1.80 (m, 3H), 1.75-1.60 (m, 2H), 1.27-1.08 (m, 4H), 1.01 (s, 9H), 094 (d, J=7.2 Hz, 3H), 0.86 (d, J=6.6 Hz, 3H); $^{13}$C NMR (CDCl$_3$, 75 MHz) δ=183.2, 171.1, 170.5, 140.1, 128.5 (2C), 128.3 (2C), 127.1, 67.2, 61.1, 60.2, 53.8, 51.7, 37.4, 35.7, 34.8, 32.5, 31.9, 31.7, 27.2 (3C), 24.7, 24.6, 19.9, 17.7; HRMS (ES) Calcd. for C$_{21}$H$_{35}$N$_4$OS [MH$^+$] m/z 391.2532, found 391.2529; HRMS (ES) Calcd. for C$_{27}$H$_{46}$N$_5$O$_2$S [MH$^+$] m/z 504.3372, found 504.3374.

Example 5

1-(3,5-bis(trifluoromethyl)phenyl)-3-((1R,2R)-2-(4-methoxybenzylamino)cyclohexyl)thiourea

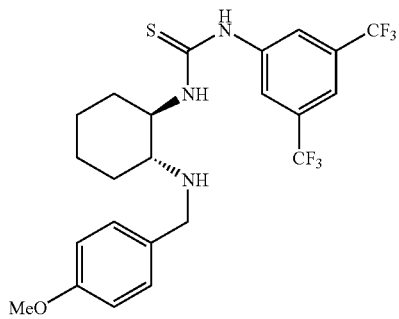

This compound was synthesized in the same manner as Example 1, except 4-methoxybenzaldehyde was used instead of benzaldehyde (40% yield).

Example 6

1-(3,5-bis(trifluoromethyl)phenyl)-3-((1R,2R)-2-(4-nitrobenzylamino)cyclohexyl)thiourea

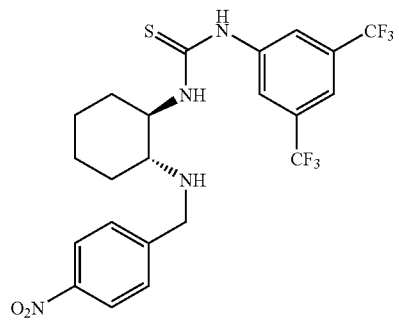

This compound was synthesized in the same manner as Example 1, except 4-nitrobenzaldehyde was used instead of benzaldehyde (48% yield).

Example 7

1-(3,5-bis(trifluoromethyl)phenyl)-3-((1R,2R)-2-(2-bromobenzylamino)cyclohexyl)thiourea

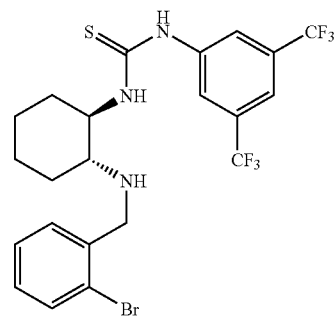

This compound was synthesized in the same manner as Example 1, except 2-bromobenzaldehyde was used instead of benzaldehyde (40% yield).

Example 8

1-(3,5-bis(trifluoromethyl)phenyl)-3-((1R,2R)-2-(2,4-dimethoxybenzylamino)cyclohexyl)thiourea

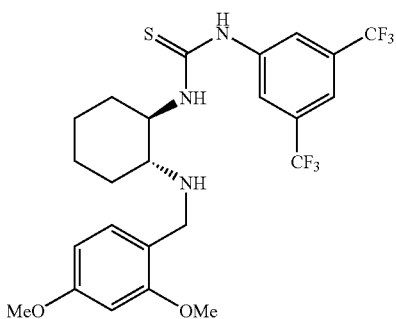

This compound was synthesized in the same manner as Example 1, except 2,4-dimethoxybenzaldehyde was used instead of benzaldehyde (47% yield).

Example 9

1-((1R,2R)-2-(benzylamino)cyclohexyl)-3-phenylthiourea

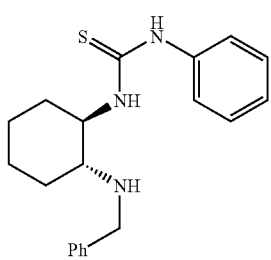

This compound was synthesized in the same manner as Example 1, except isothiocyanatobenzene was used instead of 3,5-bis(trifluoromethyl)-phenyl isothiocyanate (57% yield).

Example 10

1-((1R,2R)-2-(benzylamino)cyclohexyl)-3-(perfluorophenyl)thiourea

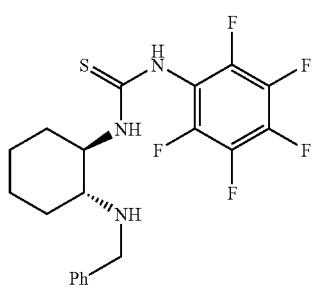

This compound was synthesized in the same manner as Example 1, except 1,2,3,4,5-pentafluoro-6-isothiocyanatobenzene was used instead of 3,5-bis(trifluoromethyl)-phenyl isothiocyanate (57% yield).

Example 11

1-((1R,2R)-2-(benzylamino)cyclohexyl)-3-(4-methoxyphenyl)thiourea

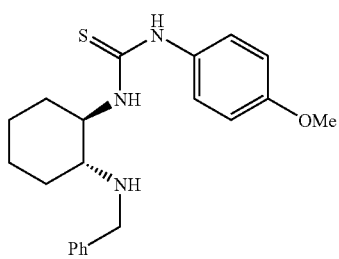

This compound was synthesized in the same manner as Example 1, except 1-isothiocyanato-4-methoxybenzene was used instead of 3,5-bis(trifluoromethyl)-phenyl isothiocyanate (57% yield).

Example 12

1-((1R,2R)-2-(benzylamino)cyclohexyl)-3-(4-nitrophenyl)thiourea

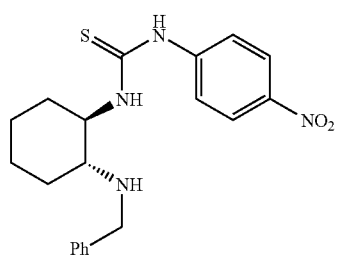

This compound was synthesized in the same manner as Example 1, except 1-isothiocyanato-4-nitrobenzene was used instead of 3,5-bis(trifluoromethyl)-phenyl isothiocyanate (47% yield).

Example 13

1-((1R,2R)-2-(benzylamino)cyclohexyl)-3-cyclohexylthiourea

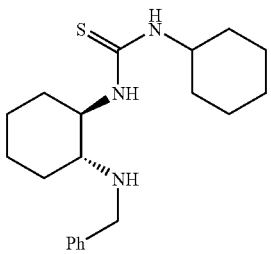

This compound was synthesized in the same manner as Example 1, except isothiocyanatocyclohexane was used instead of 3,5-bis(trifluoromethyl)-phenyl isothiocyanate (57% yield).

Example 14

1-((1R,2R)-2-(benzylamino)cyclohexyl)-3-methylthiourea

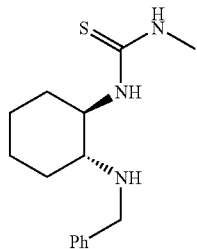

This compound was synthesized in the same manner as Example 1, except isothiocyanatomethane was used instead of 3,5-bis(trifluoromethyl)-phenyl isothiocyanate (45% yield).

Example 15

1-(3,5-bis(trifluoromethyl)phenyl)-3-((1R,2R)-2-(naphthalen-1-ylmethylamino)cyclohexyl)thiourea

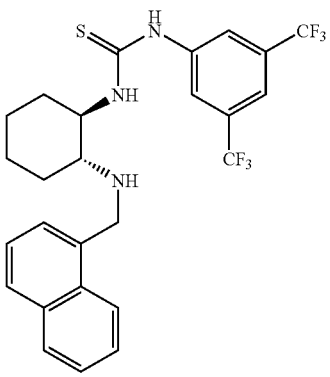

This compound was synthesized in the same manner as Example 1, except 1-naphthaldehyde was used instead of benzaldehyde (54% yield).

Example 16

1-(3,5-bis(trifluoromethyl)phenyl)-3-((1R,2R)-2-(naphthalen-2-ylmethylamino)cyclohexyl)thiourea

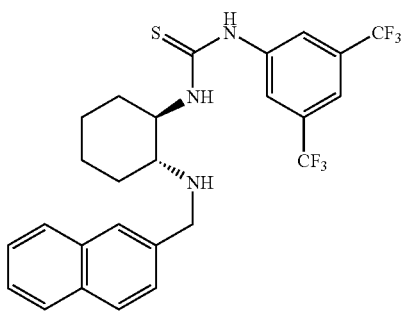

This compound was synthesized in the same manner as Example 1, except 2-naphthaldehyde was used instead of benzaldehyde (54% yield).

Example 17

1-((1S,2S)-2-(benzylamino)-1,2-diphenylethyl)-3-(3,5-bis(trifluoromethyl)phenyl)thiourea

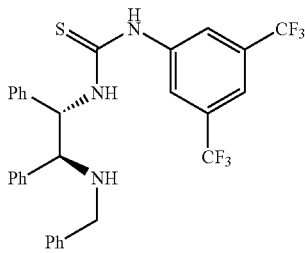

This compound was synthesized in the same manner as Example 1, except (1S,2S)-1,2-diphenylethane-1,2-diamine was used instead of (R,R)-cyclohexanediamine (54% yield).

Example 18

1-((1R,2R)-2-(benzylamino)cyclohexyl)-3-((R)-1-(naphthalen-1-yl)ethyl)thiourea

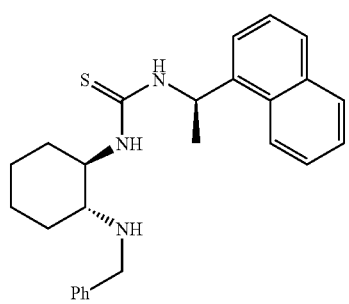

This compound was synthesized in the same manner as Example 1, except (R)-1-(1-isothiocyanatoethyl)naphthalene was used instead of 3,5-bis(trifluoromethyl)-phenyl isothiocyanate (55% yield).

Example 19

1-((1R,2R)-2-(benzylamino)cyclohexyl)-3-((S)-1-(naphthalen-1-yl)ethyl)thiourea

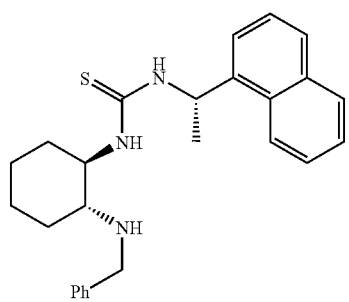

This compound was synthesized in the same manner as Example 1, except (S)-1-(1-isothiocyanatoethyl)naphthalene was used instead of 3,5-bis(trifluoromethyl)-phenyl isothiocyanate (48% yield).

Example 20

(S)-2-(3-((1S,2S)-2-(benzylamino)cyclohexyl)thio-ureido)-N,3,3-trimethylbutanamide

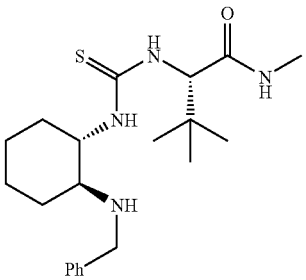

This compound was synthesized in the same manner as Example 2, except (S,S)-cyclohexanediamine was used instead of (R,R)-cyclohexanediamine (48% yield).

Example 21

(S)-2-(3-((1R,2R)-2-(benzylamino)cyclohexyl)thio-ureido)-N-tert-butyl-3,3-dimethylbutanamide

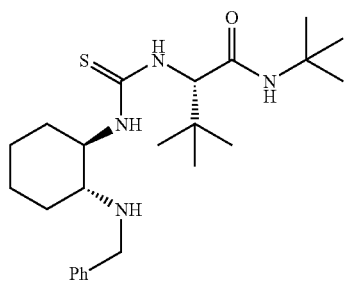

This compound was synthesized in the same manner as Example 1, except (S)—N-tert-butyl-2-isothiocyanato-3,3-dimethylbutanamide was used instead of 3,5-bis(trifluoromethyl)-phenyl isothiocyanate. 54% yield.

Example 22

(S)-2-(3-((1S,2S)-2-(benzylamino)cyclohexyl)thio-ureido)-N-tert-butyl-3,3-dimethylbutanamide

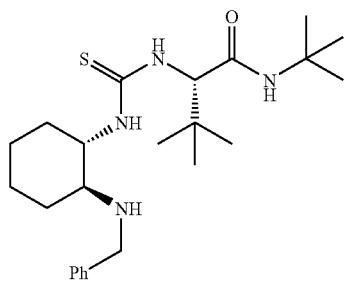

This compound was synthesized in the same manner as Example 21, except (S,S)-cyclohexanediamine was used instead of (R,R)-cyclohexanediamine (53% yield).

Example 23

(S)—N-benzyl-2-(3-((1S,2S)-2-(benzylamino)cyclo-hexyl)thioureido)-N,3,3-trimethylbutanamide

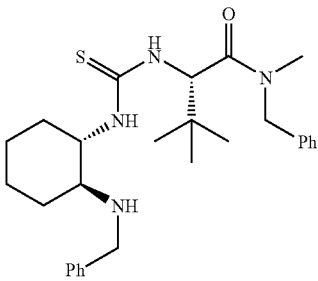

This compound was synthesized in the same manner as Example 3, except (S,S)-cyclohexanediamine was used instead of (R,R)-cyclohexanediamine (43% yield).

Example 24

1-((1R,2R)-2-(benzylamino)cyclohexyl)-3-((1R,2R,3R,5S)-2,6,6-trimethylbicyclo[3.1.1]heptan-3-yl)thiourea

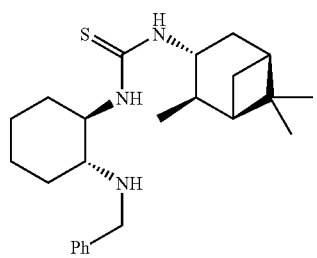

This compound was synthesized in the same manner as Example 1, except (1R,2R,3R,5S)-3-isothiocyanato-2,6,6-trimethylbicyclo[3.1.1]heptane was used instead of 3,5-bis(trifluoromethyl)-phenyl isothiocyanate (48% yield).

Example 25

1-((1S,2S)-2-(benzylamino)cyclohexyl)-3-((1R,2R,3R,5S)-2,6,6-trimethylbicyclo[3.1.1]heptan-3-yl)thiourea

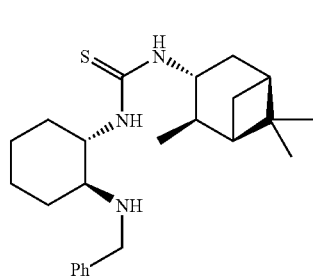

This compound was synthesized in the same manner as Example 24, except (S,S)-cyclohexanediamine was used instead of (R,R)-cyclohexanediamine (43% yield).

Example 26

(S)-2-(3-((1S,2S)-2-(benzylamino)cyclohexyl)thio-ureido)-N—((R)-1-(dimethylamino)-3-methyl-1-oxobutan-2-yl)-3,3-dimethylbutanamide

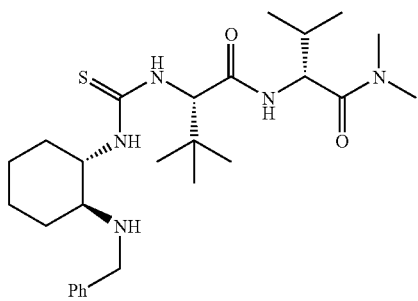

This compound was synthesized in the same manner as Example 4, except (S,S)-cyclohexanediamine was used instead of (R,R)-cyclohexanediamine (43% yield).

Example 27

(S)-2-(3-((1R,2R)-2-(benzylamino)cyclohexyl)thio-ureido)-N—((S)-1-(dimethylamino)-3-methyl-1-oxobutan-2-yl)-3,3-dimethylbutanamide

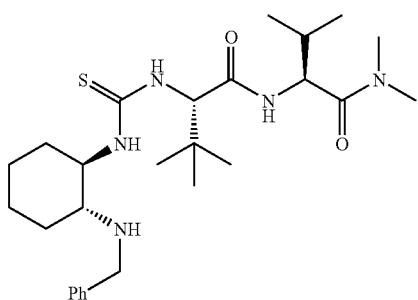

This compound was synthesized in the same manner as Example 1, except (S)—N—((S)-1-(dimethylamino)-3-methyl-1-oxobutan-2-yl)-2-isothiocyanato-3,3-dimethylbutanamide was used instead of 3,5-bis(trifluoromethyl)-phenyl isothiocyanate (48% yield).

Example 28

(S)-2-(3-((1S,2S)-2-(benzylamino)cyclohexyl)thio-ureido)-N—((S)-1-(dimethylamino)-3-methyl-1-oxobutan-2-yl)-3,3-dimethylbutanamide

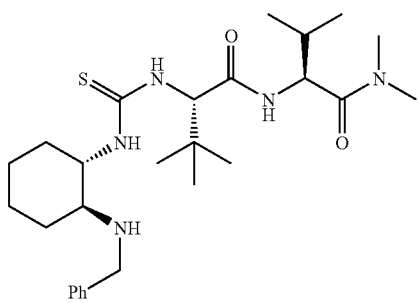

This compound was synthesized in the same manner as Example 27, except (S,S)-cyclohexanediamine was used instead of (R,R)-cyclohexanediamine (53% yield).

Example 29

1-((1R,2R)-2-(benzylamino)cyclohexyl)-3-((S)-3,3-dimethyl-1-oxo-1-(piperidin-1-yl)butan-2-yl)thiourea

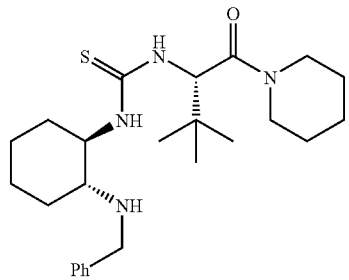

This compound was synthesized in the same manner as Example 1, except (S)-2-isothiocyanato-3,3-dimethyl-1-(piperidin-1-yl)butan-1-one was used instead of 3,5-bis(trifluoromethyl)-phenyl isothiocyanate (56% yield).

Example 30

1-((1S,2S)-2-(benzylamino)cyclohexyl)-3-((S)-3,3-dimethyl-1-oxo-1-(piperidin-1-yl)butan-2-yl)thiourea

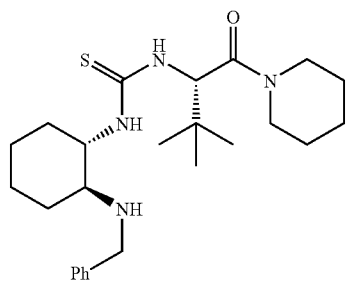

This compound was synthesized in the same manner as Example 29, except (S,S)-cyclohexanediamine was used instead of (R,R)-cyclohexanediamine (53% yield).

Example 31

(S)—N-benzyl-2-(3-((1R,2R)-2-(benzylamino)cyclohexyl)thioureido)-N-methylpropanamide

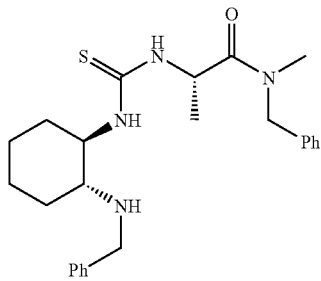

This compound was synthesized in the same manner as Example 1, except ((S)—N-benzyl-2-isothiocyanato-N-methylpropanamide was used instead of 3,5-bis(trifluoromethyl)-phenyl isothiocyanate (56% yield).

Example 32

(S)—N-benzyl-2-(3-((1S,2S)-2-(benzylamino)cyclo-hexyl)thioureido)-N-methylpropanamide

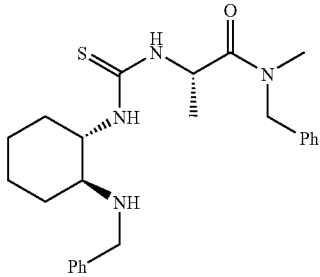

This compound was synthesized in the same manner as Example 31, except (S,S)-cyclohexanediamine was used instead of (R,R)-cyclohexanediamine (46% yield).

Example 33

(S)—N,N-dibenzyl-2-(3-((1R,2R)-2-(benzylamino)cyclohexyl)thioureido)-3,3-dimethylbutanamide

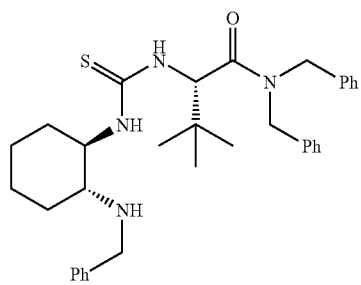

This compound was synthesized in the same manner as Example 1, except (S)—N,N-dibenzyl-2-isothiocyanato-3,3-dimethylbutanamide was used instead of 3,5-bis(trifluoromethyl)-phenyl isothiocyanate (51% yield).

Example 34

(S)—N,N-dibenzyl-2-(3-((1S,2S)-2-(benzylamino)cyclohexyl)thioureido)-3,3-dimethylbutanamide:

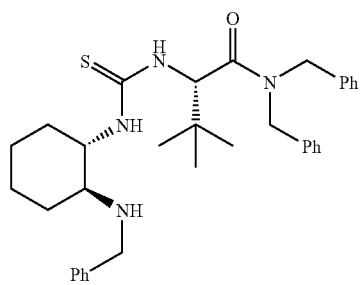

This compound was synthesized in the same manner as Example 33, except (S,S)-cyclohexanediamine was used instead of (R,R)-cyclohexanediamine (61% yield).

Example 35

(S)—N-benzyl-2-(3-((1R,2R)-2-(benzylamino)cyclohexyl)thioureido)-N,4-dimethylpentanamide

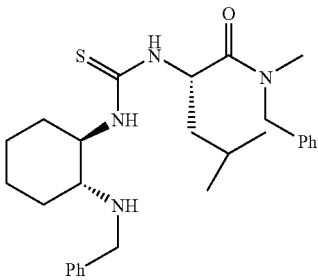

This compound was synthesized in the same manner as Example 1, except (S)—N-benzyl-2-isothiocyanato-N,4-dimethylpentanamide was used instead of 3,5-bis(trifluoromethyl)-phenyl isothiocyanate (51% yield).

Example 36

(S)—N-benzyl-2-(3-((1S,2S)-2-(benzylamino)cyclohexyl)thioureido)-N,4-dimethylpentanamide

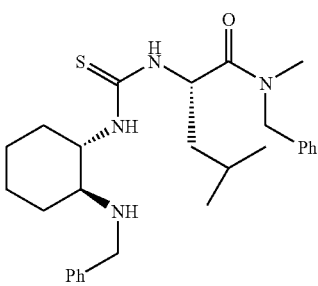

This compound was synthesized in the same manner as Example 35, except (S,S)-cyclohexanediamine was used instead of (R,R)-cyclohexanediamine (41% yield).

Example 37

(S)—N-benzyl-2-(3-((1R,2R)-2-(benzylamino)cyclohexyl)thioureido)-N-methyl-3-phenylpropanamide

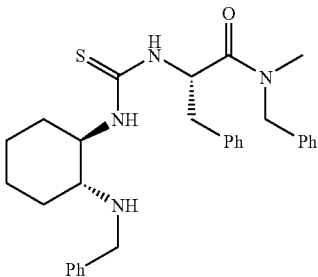

This compound was synthesized in the same manner as Example 1, except (S)—N-benzyl-2-isothiocyanato-N-methyl-3-phenylpropanamide was used instead of 3,5-bis(trifluoromethyl)-phenyl isothiocyanate (51% yield).

Example 38

(S)—N-benzyl-2-(3-((1S,2S)-2-(benzylamino)cyclohexyl)thioureido)-N-methyl-3-phenylpropanamide

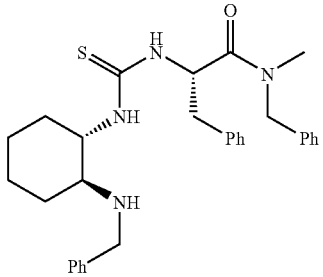

This compound was synthesized in the same manner as Example 37, except (S,S)-cyclohexanediamine was used instead of (R,R)-cyclohexanediamine (39% yield).

Catalytic Reduction of Prochiral Ketones

Example 39

Figure 7:
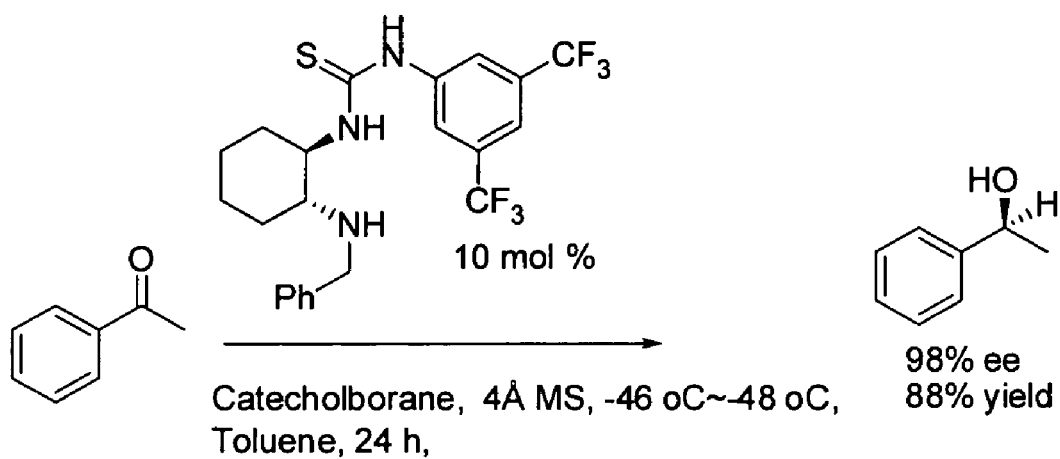
FIG. 7 shows a general scheme for the synthesis of (S)-1-phenylethanol.

(S)-1-phenylethanol was synthesized as shown in FIG. 7. Thiourea (12 mg, 0.025 mmol), which was obtained as shown in Example 1, and 4 Å molecular sieve, which was freshly dried by flame under vacuum for 30 min and cooled under argon, 250 mg, were added to an oven-dried vial and flushed with argon three times. Toluene (0.7 mL) was added to the mixture, followed by acetophenone (30 mg, 0.25 mmol). The mixture was cooled to −78° C. and a solution of catecholborane (1.0 M in Toluene, 0.4 mL, 0.4 mmol) was added slowly along the side of the vial. The resulting reaction mixture was put into a −46° C.~−48° C. bath. After stirring for 24 hours at −46° C.~−48° C., MeOH (1 mL) was added followed by 3 N NaOH (1 mL). The mixture was gradually warmed to room temperature and stirred for another 1 hour at room temperature, and then extracted with ether (10 mL×3), dried over $Na_2SO_4$ and concentrated in vacuo. The residue was purified by flash column chromatography on silica gel using Hexanes/EtOAc (6:1) as eluent to give (S)-1-phenylethanol as colorless oil (27 mg, 88% yield); 98% ee, HPLC analysis (Chiralcel OD, 250 mm×4.6 mm, 2% iPrOH/Hexane, 1.0 mL/min, 254 nm; $t_r$(major)=19.2 min, $t_r$(minor)=15.0 min); $[\alpha]^{20}_D$=−51.7 (c 1.09, $CHCl_3$, lit. (Sokeirik 2007) (R)-1-phenylethanol, 96% ee, $[\alpha]_D$=+42.92 (c 1.04, $CHCl_3$)); $^1H$ NMR ($CDCl_3$, 300 MHz) δ=7.38-7.23 (m, 5H), 4.87 (q, J=6.3 Hz, 1H), 2.03 (br s, 1H), 1.90 (d, J=6.3 Hz, 3H); $^{13}C$ NMR ($CDCl_3$, 75 MHz) δ=145.9, 128.6 (2C), 127.6, 125.5 (2C), 70.5, 25.3.

Figure 8:
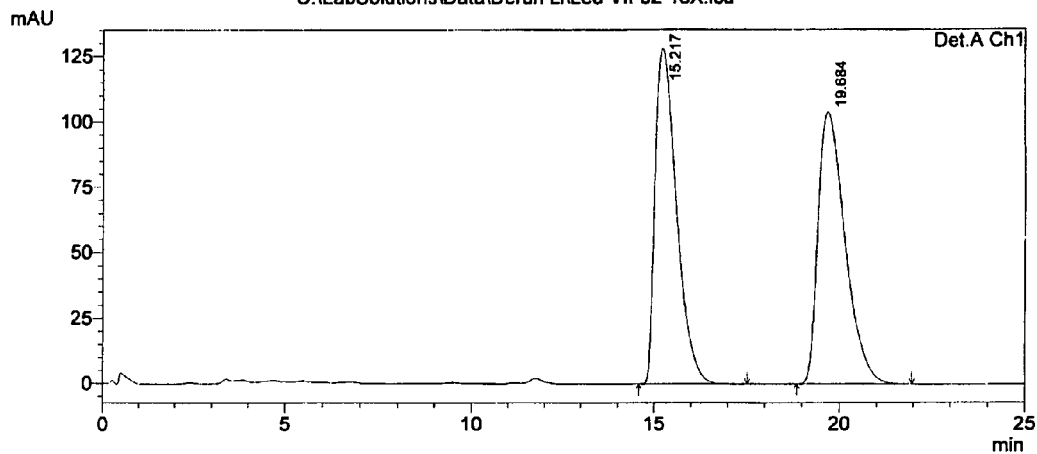
FIG. 8 shows the HPLC analysis for (S)-1-phenylethanol (Chiralcel OD, 250 mm×4.6 mm, 2% iPrOH/Hexane, 1.0 mL/min, 254 nm).
Figure 8:
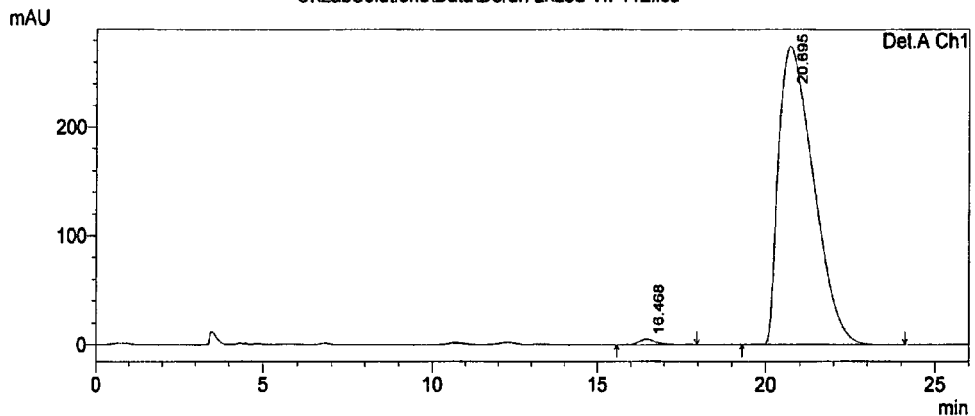

The HPLC analysis for (S)-1-phenylethanol (Chiralcel OD, 250 mm×4.6 mm, 2% iPrOH/Hexane, 1.0 mL/min, 254 nm) is shown in FIG. 8.

Example 40

(S)-1-phenylpropan-1-ol

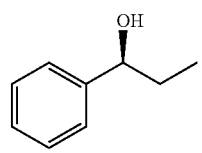

This compound was synthesized in the same manner as Example 39, except propiophenone was used instead of acetophenone. 86% yield, 99% ee, HPLC analysis (Chiralcel OD, 250 mm×4.6 mm, 2% iPrOH in Hexane, 1.0 mL/min, 254 nm; $t_r$(major)=17.3 min, $t_r$(minor)=14.4 min); $[\alpha]^{20}_D$=−47.4 (c 1.48, $CHCl_3$, lit. (Lutz 1997) (S)-1-phenylpropan-1-ol, 98% ee, $[\alpha]^{25}_D$=−48.4 (c 2.31, $CHCl_3$)); $^1H$ NMR ($CDCl_3$, 300 MHz) δ=7.38-7.26 (m, 5H), 4.57 (t, J=6.3 Hz, 1H), 2.25 (br s, 1H), 1.87-1.69 (m, 2H), 0.91 (t, J=7.8 Hz, 3H); $^{13}C$ NMR ($CDCl_3$, 75 MHz) δ=145.0, 128.5 (2C), 127.6, 126.1 (2C), 74.5, 41.3, 19.1, 14.1.

Figure 9:
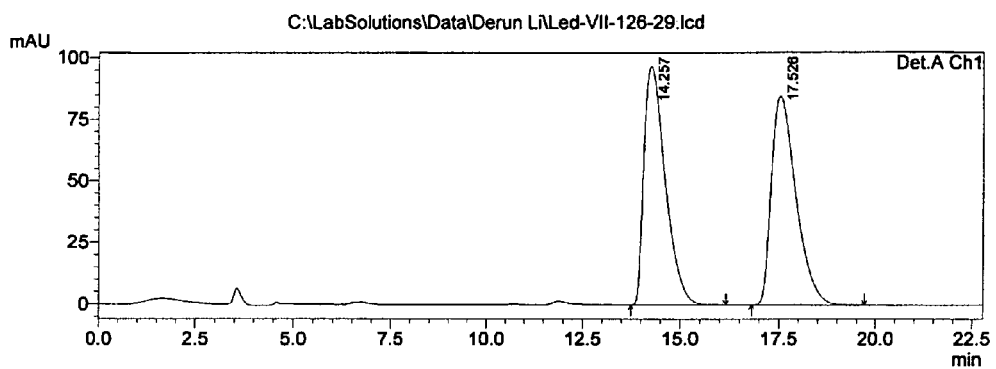
FIG. 9 shows the HPLC analysis for (S)-1-phenylpropan-1-ol (Chiralcel OD, 250 mm×4.6 mm, 2% iPrOH in Hexane, 1.0 mL/min, 254 nm).
Figure 9:
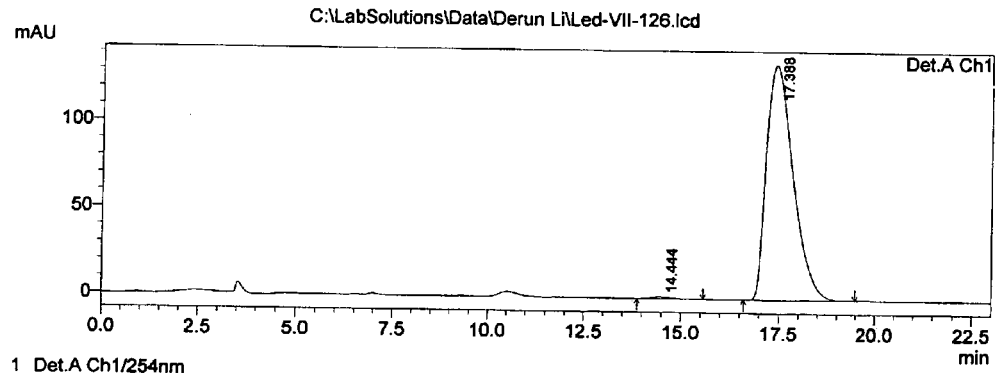

The HPLC analysis for (S)-1-phenylpropan-1-ol (Chiralcel OD, 250 mm×4.6 mm, 2% iPrOH in Hexane, 1.0 mL/min, 254 nm) is shown in FIG. 9.

Example 41

(S)-1-phenylbutan-1-ol

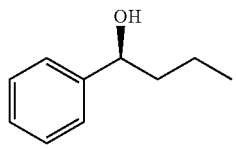

This compound was synthesized in the same manner as Example 39, except the 1-phenylbutan-1-one was used instead of acetophenone. 81% yield, 99% ee, HPLC analysis (Chiralcel OD, 250 mm×4.6 mm, 1% iPrOH in Hexane, 1.0 mL/min, 254 nm; $t_r$(major)=23.8 min, $t_r$(minor)=21.8 min); $[\alpha]^{20}_D$=−47.6 (c 0.50, $CHCl_3$, lit. (R)-1-phenylbutan-1-ol, 93% ee, $[\alpha]^{24}_D$=+42 (c 0.28, $CHCl_3$)); $^1H$ NMR ($CDCl_3$, 300 MHz) δ=7.38-7.26 (m, 5H), 4.64 (t, J=6.3 Hz, 1H), 2.21 (br s, 1H), 1.83-1.63 (m, 2H), 1.47-1.26 (m, 2H), 0.93 (t, J=7.2 Hz, 3H); $^{13}C$ NMR ($CDCl_3$, 75 MHz) δ=144.7, 128.5 (2C), 127.6, 126.1 (2C), 76.1, 31.9, 10.2.

Figure 10:
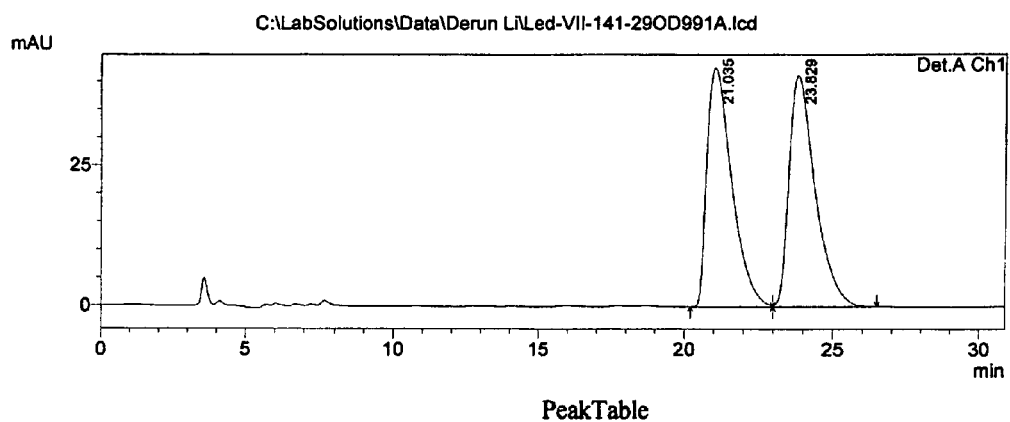
FIG. 10 shows the HPLC analysis for (S)-1-phenylbutan-1-ol (Chiralcel OD, 250 mm×4.6 mm, 1% iPrOH in Hexane, 1.0 mL/min, 254 nm).
Figure 10:
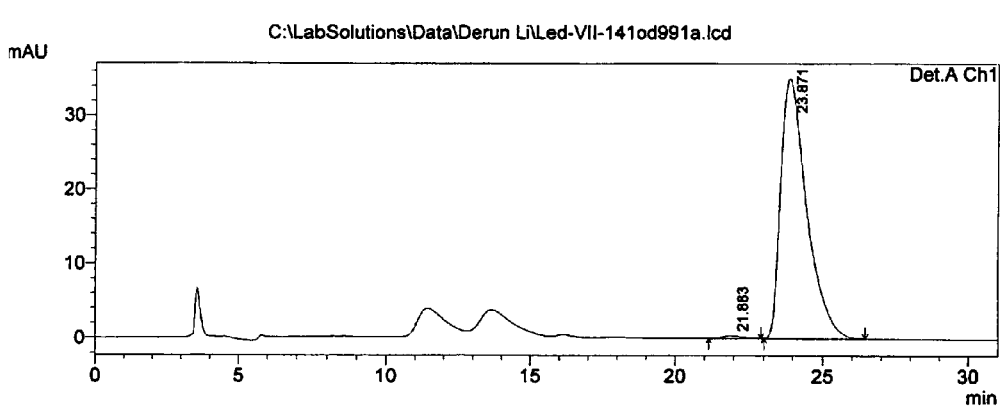

The HPLC analysis for (S)-1-phenylbutan-1-ol (Chiralcel OD, 250 mm×4.6 mm, 1% iPrOH in Hexane, 1.0 mL/min, 254 nm) is shown in FIG. 10.

Example 42

(S)-1-o-tolylethanol

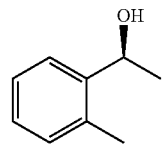

This compound was synthesized in the same manner as Example 39, except the reaction time was 26 h and 1-o-tolylethanone was used instead of acetophenone. 71% yield, 95% ee, HPLC analysis (Chiralpak AD, 250 mm×4.6 mm, 2% iPrOH in Hexane, 0.5 mL/min, 254 nm; $t_r$(major)=24.4 min, $t_r$(minor)=21.8 min); $[\alpha]^{20}_D$=−70.0 (c 1.0, $CHCl_3$, lit. (Node 2000) (S)-1-o-tolylethanol, 99% ee, $[\alpha]^{25}_D$=−39.7 (c 0.56, $CHCl_3$)); $^1H$ NMR ($CDCl_3$, 300 MHz) δ=7.52-7.49 (m, 1H), 7.27-7.12 (m, 3H), 5.10 (q, J=6.3 Hz, 1H), 2.34 (s, 3H), 2.16 (br s, 1H), 1.45 (d, J=6.3 Hz, 3H); $^{13}C$ NMR ($CDCl_3$, 75 MHz) δ=143.9, 134.2, 130.4, 127.2, 126.4, 124.5, 66.8, 24.0, 19.0.

Figure 11:
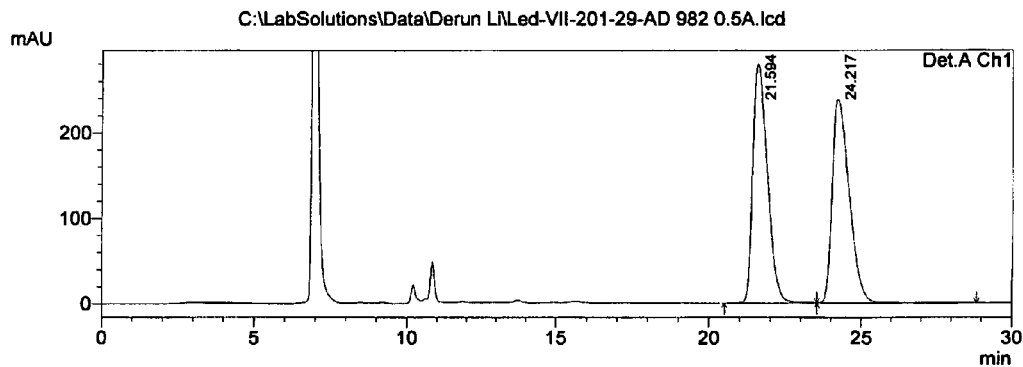
FIG. 11 shows the HPLC analysis for (S)-1-o-tolylethanol (Chiralpak AD, 250 mm×4.6 mm, 2% iPrOH in Hexane, 0.5 mL/min, 254 nm).
Figure 11:
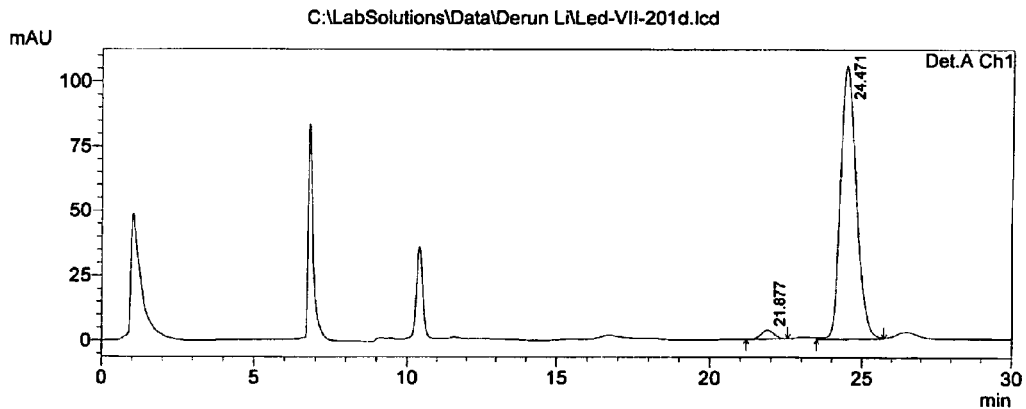

The HPLC analysis for (S)-1-o-tolylethanol (Chiralpak AD, 250 mm×4.6 mm, 2% iPrOH in Hexane, 0.5 mL/min, 254 nm) is shown in FIG. 11.

Example 43

(S)-1-(3-(trifluoromethyl)phenyl)ethanol

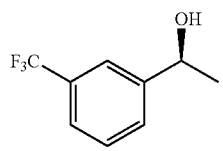

This compound was synthesized in the same manner as Example 39, except the reaction time was 22 h and 1-(3-(trifluoromethyl)phenyl)ethanone was used instead of acetophenone. 92% yield, 96% ee, HPLC analysis (Chiralcel OD, 250 mm×4.6 mm, 2% iPrOH in Hexane, 1.0 mL/min, 254 nm; $t_r$(major)=14.0 min, $t_r$(minor)=17.6 min); $[\alpha]^{20}_D$=−31.0 (c 1.95, CHCl$_3$, lit. (Tanaka 2000) (S)-1-(3-(trifluoromethyl)phenyl)ethanol, >99% ee, $[\alpha]^{20}_D$=−27.9 (c 1.64 in CH$_3$OH)); $^1$H NMR (CDCl$_3$, 300 MHz) δ=7.63 (d, J=0.6 Hz, 1H), 7.54-7.42 (m, 3H), 4.93 (q, J=6.3 Hz, 1H), 2.33 (br s, 1H), 1.48 (d, J=6.3 Hz, 3H); $^{13}$C NMR (CDCl$_3$, 75 MHz) δ=146.8, 131.0 (q, $J_{CF}$=32.1 Hz), 129.1, 128.9, 124.4, 124.3, 122.4, 69.9, 25.4.

Figure 12:
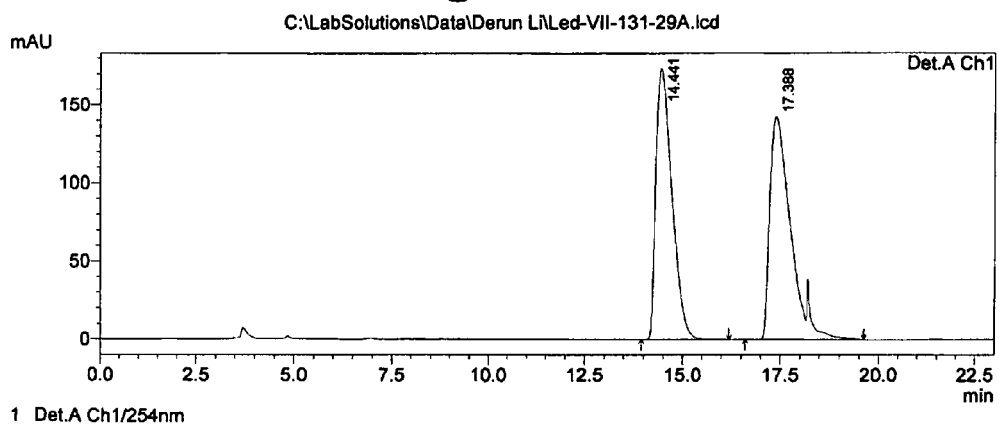
FIG. 12 shows the HPLC analysis for (S)-1-(3-(trifluoromethyl)phenyl)ethanol (Chiralcel OD, 250 mm×4.6 mm, 2% iPrOH in Hexane, 1.0 mL/min, 254 nm).
Figure 12:
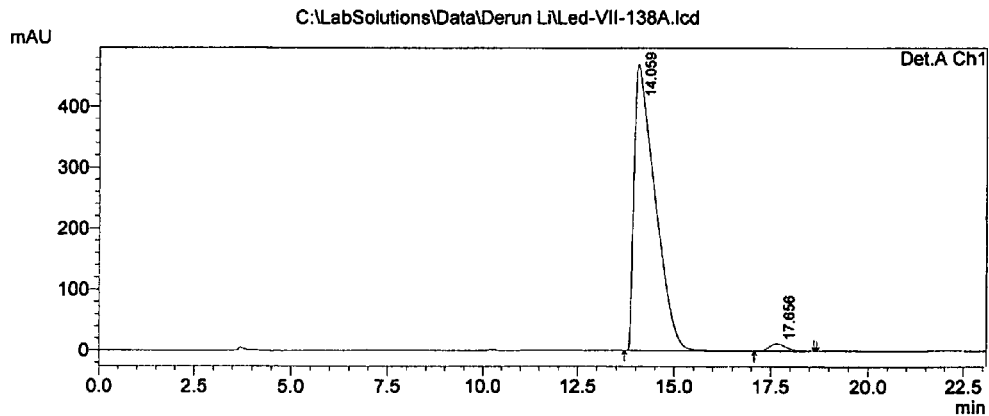

The HPLC analysis for (S)-1-(3-(trifluoromethyl)phenyl)ethanol (Chiralcel OD, 250 mm×4.6 mm, 2% iPrOH in Hexane, 1.0 mL/min, 254 nm) is shown in FIG. 12.

Example 44

(S)-1-(4-methoxyphenyl)ethanol

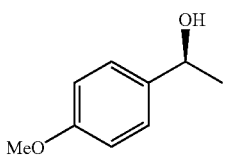

This compound was synthesized in the same manner as Example 39, except the reaction time was 36 hours and 1-(4-methoxyphenyl)ethanone was used instead of acetophenone. 80% yield, 97% ee, HPLC analysis (Chiralcel OB, 250 mm×4.6 mm, 10% iPrOH in Hexane, 0.5 mL/min, 254 nm; $t_r$(major)=21.2 min, $t_r$(minor)=18.6 min); $[\alpha]^{20}_D$=−52.3 (c 1.55, CHCl$_3$, lit. (R)-1-(4-methoxyphenyl)ethanol, 92% ee, $[\alpha]_D$=+40.64 (c 1.53, CHCl$_3$)); $^1$H NMR (CDCl$_3$, 300 MHz) δ=7.30-7.25 (m, 2H), 6.89-6.84 (m, 2H), 4.82 (q, J=6.6 Hz, 1H), 3.79 (s, 3H), 2.22 (br s, 1H), 1.46 (d, J=6.6 Hz, 3H); $^{13}$C NMR (CDCl$_3$, 75 MHz) δ=159.0, 138.1, 126.8 (2C), 113.9 (2C), 70.0, 55.4, 25.1.

Figure 13:
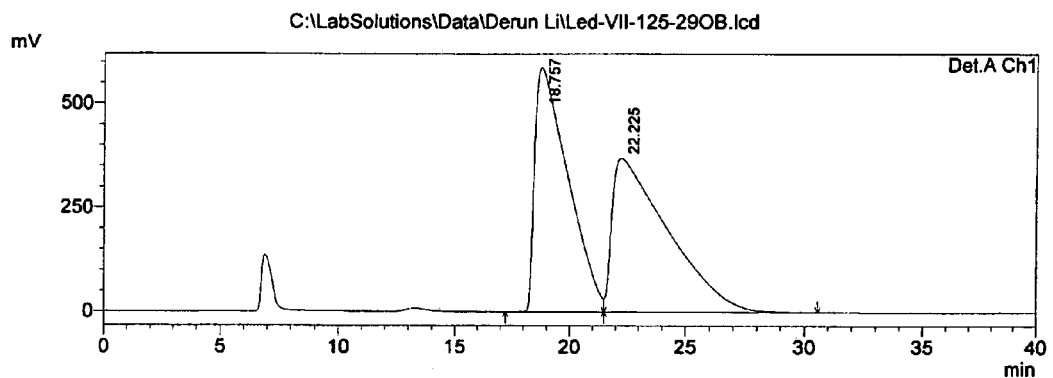
FIG. 13 shows the HPLC analysis for (S)-1-(4-methoxyphenyl)ethanol (Chiralcel OB, 250 mm×4.6 mm, 10% iPrOH in Hexane, 0.5 mL/min, 254 nm).
Figure 13:
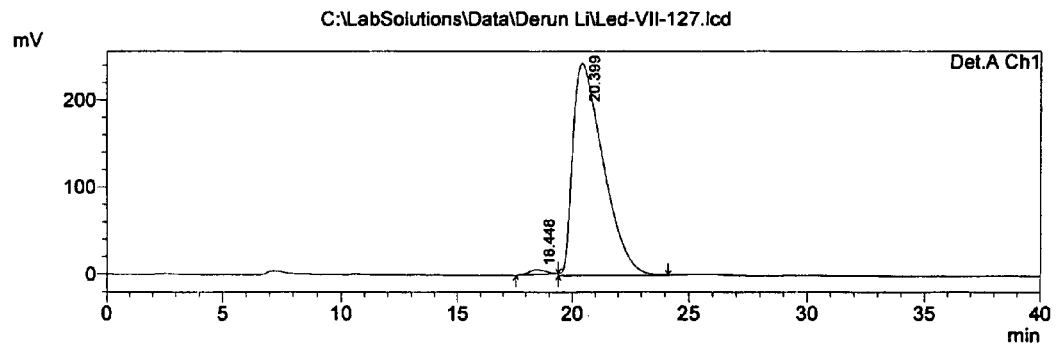

The HPLC analysis for (S)-1-(4-methoxyphenyl)ethanol (Chiralcel OB, 250 mm×4.6 mm, 10% iPrOH in Hexane, 0.5 mL/min, 254 nm) is shown in FIG. 13.

Example 45

(S)-1-(4-fluorophenyl)ethanol

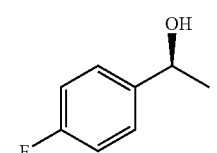

In the same manner of Example 39, except the reaction time was 20 h and 1-(4-fluorophenyl)ethanone was used instead of acetophenone. 84% yield, 99% ee, HPLC analysis (Chiralcel OB, 250 mm×4.6 mm, 1% iPrOH in Hexane, 0.6 mL/min, 254 nm; $t_r$(major)=36.4 min, $t_r$(minor)=43.0 min); $[\alpha]^{20}_D$=−44.8 (c 1.40, CHCl$_3$, lit. Carter 1994 (S)-1-(4-fluorophenyl)ethanol, 97% ee, $[\alpha]_D$=−47.5 (c 0.0576, CHCl$_3$)); $^1$H NMR (CDCl$_3$, 300 MHz) δ=7.34-7.26 (m, 2H), 7.05-7.6.98 (m, 2H), 4.84 (q, J=6.6 Hz, 1H), 2.27 (br s, 1H), 1.45 (d, J=6.3 Hz, 3H); $^{13}$C NMR (CDCl$_3$, 75 MHz) δ=162.2 (d, $J_{CF}$=243.8 Hz), 141.7 (d, J=3.1 Hz), 127.2 (d, J=7.9 Hz, 2C), 115.4 (d, J=21.2 Hz, 2C), 69.8, 25.4.

Figure 14:
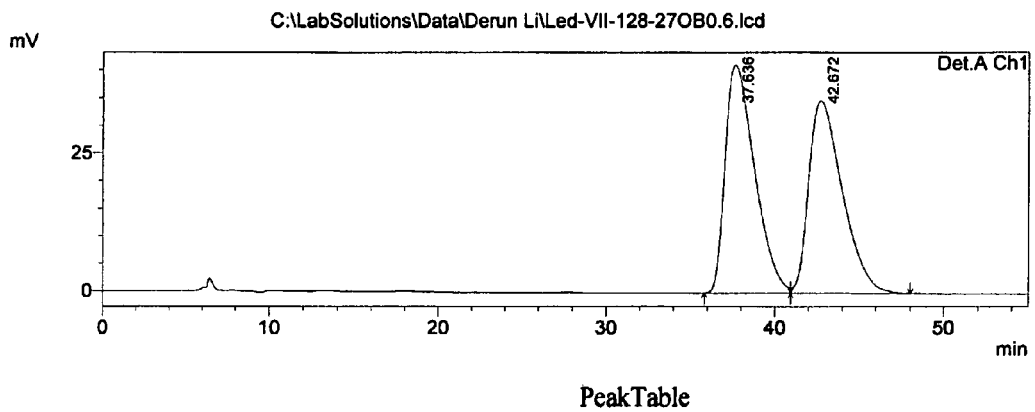
FIG. 14 shows the HPLC analysis for (S)-1-(4-fluorophenyl)ethanol (Chiralcel OB, 250 mm×4.6 mm, 1% iPrOH in Hexane, 0.6 mL/min, 254 nm).
Figure 14:
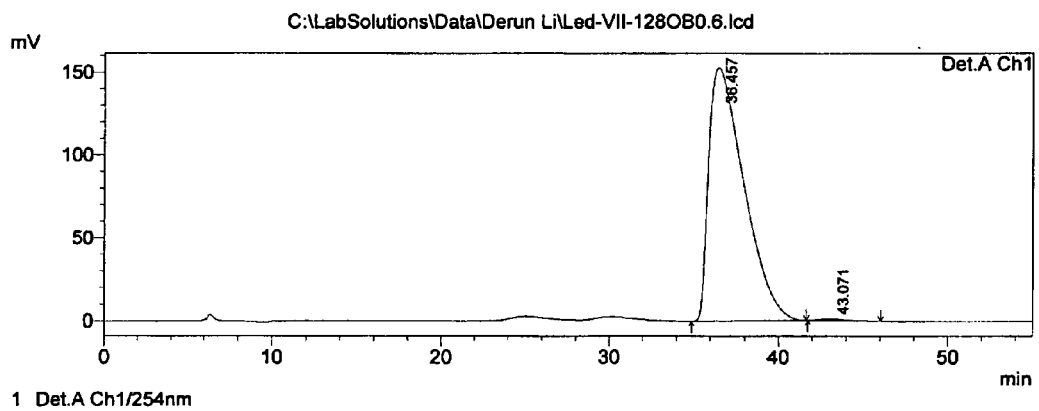

The HPLC analysis for (S)-1-(4-fluorophenyl)ethanol (Chiralcel OB, 250 mm×4.6 mm, 1% iPrOH in Hexane, 0.6 mL/min, 254 nm) is shown in FIG. 14.

Example 46

(S)-1-(4-chlorophenyl)ethanol

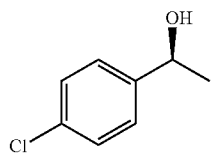

In the same manner of Example 39, except the reaction time was 22 h and 1-(4-chlorophenyl)ethanone was used instead of acetophenone. 94% yield, 99% ee, HPLC analysis (Chiralcel OB, 250 mm×4.6 mm, Hexane/EtOH (60:1), 0.5 mL/min, 254 nm; $t_r$(major)=22.1 min, $t_r$(minor)=25.8 min); $[\alpha]^{20}_D$=−44.2 (c 1.80, CHCl$_3$, lit. (Utsukihara 2006) (S)-1-(4-chlorophenyl)ethanol, 96% ee, $[\alpha]^{27}_D$=−45.0 (c 0.90, CHCl$_3$)); $^1$H NMR (CDCl$_3$, 300 MHz) δ=7.33-7.25 (m, 4H), 4.86 (q, J=6.0 Hz, 1H), 2.00 (br s, 1H), 1.43 (d, J=6.0 Hz, 3H); $^{13}$C NMR (CDCl$_3$, 75 MHz) δ=144.4, 133.2, 128.7 (2C), 126.9 (2C), 69.9, 25.4.

Figure 15:
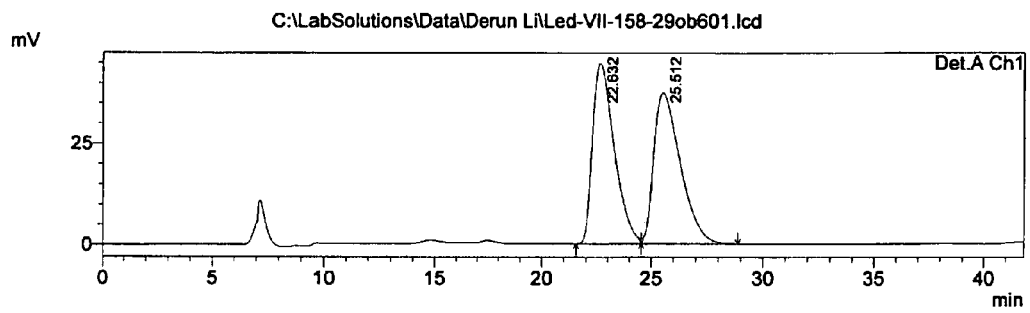
FIG. 15 shows the HPLC analysis for (S)-1-(4-chlorophenyl)ethanol (Chiralcel OB, 250 mm×4.6 mm, Hexane/EtOH (60:1), 0.5 mL/min, 254 nm).
Figure 15:
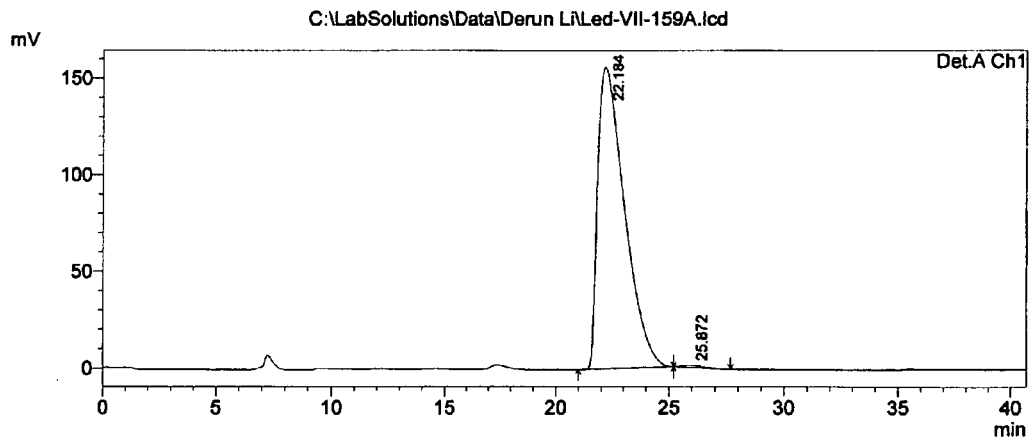

The HPLC analysis for (S)-1-(4-chlorophenyl)ethanol (Chiralcel OB, 250 mm×4.6 mm, Hexane/EtOH (60:1), 0.5 mL/min, 254 nm) is shown in FIG. 15.

Example 47

(S)-1-(4-bromophenyl)ethanol

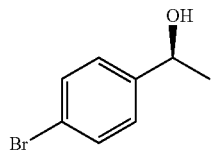

This compound was synthesized in the same manner as Example 39, except the reaction time was 22 hours and 1-(4-bromophenyl)ethanone was used instead of acetophenone. 95% yield, 99% ee, HPLC analysis (Chiralcel OB, 250 mm×4.6 mm, Hexane/EtOH (60:1), 0.5 mL/min, 254 nm; $t_r$(major)=24.5 min, $t_r$(minor)=28.9 min); $[\alpha]^{20}_D$=−36.9 (c 2.40, CHCl$_3$, lit. (S)-1-(4-bromophenyl)ethanol, 98% ee, $[\alpha]^{27}_D$=−37.3 (c 1.1, CHCl$_3$)); $^1$H NMR (CDCl$_3$, 300 MHz) δ=7.48-7.44 (m, 2H), 7.26-7.21 (m, 2H), 4.84 (q, J=6.3 Hz, 1H), 2.02 (br s, 1H), 1.46 (d, J=6.3 Hz, 3H); $^{13}$C NMR (CDCl$_3$, 75 MHz) δ=144.9, 131.7 (2C), 127.3 (2C), 121.3, 69.9, 25.4.

Figure 16:
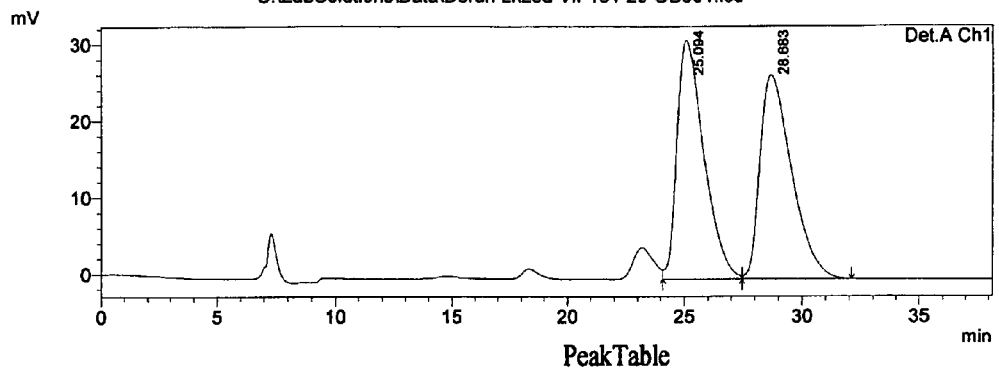
FIG. 16 shows the HPLC analysis for (S)-1-(4-bromophenyl)ethanol (Chiralcel OB, 250 mm×4.6 mm, Hexane/EtOH (60:1), 0.5 mL/min, 254 nm).
Figure 16:
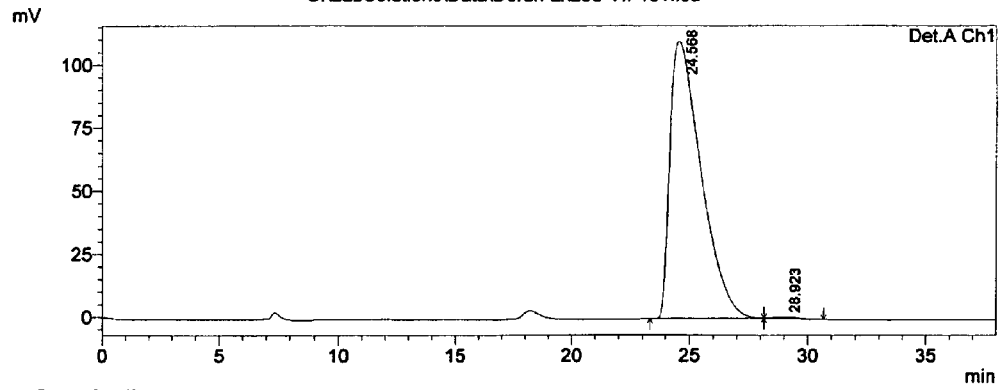

The HPLC analysis for (S)-1-(4-bromophenyl)ethanol (Chiralcel OB, 250 mm×4.6 mm, Hexane/EtOH (60:1), 0.5 mL/min, 254 nm) is shown in FIG. 16.

Example 48

(S)-1,2,3,4-tetrahydronaphthalen-1-ol

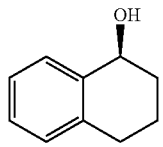

This compound was synthesized in the same manner as Example 39, except 3,4-dihydronaphthalen-1(2H)-one was used instead of acetophenone. 86% yield, 99% ee, HPLC analysis (Chiralcel OD, 250 mm×4.6 mm, 2% iPrOH in Hexane, 1.0 mL/min, 254 nm; $t_r$(major)=16.2 min, $t_r$(minor)=18.6 min); $[\alpha]^{20}{}_D$=38.9 (c 1.45, CHCl$_3$, lit. (S)-1,2,3,4-tetrahydronaphthalen-1-ol, 91% ee, $[\alpha]^{25}{}_D$=31.2 (c 0.54, CHCl$_3$)); $^1$H NMR (CDCl$_3$, 300 MHz) δ=7.44-7.41 (m, 1H), 7.23-7.19 (m, 2H), 7.12-7.10 (m, 1H), 4.77 (t, J=4.5 Hz, 1H), 2.88-2.68 (m, 2H), 2.05 (br s, 1H), 2.02-1.75 (m, 4H); $^{13}$C NMR (CDCl$_3$, 75 MHz) δ=138.9, 137.2, 129.1, 128.8, 127.6, 126.3, 68.2, 32.3, 29.3, 18.9.

Figure 17:
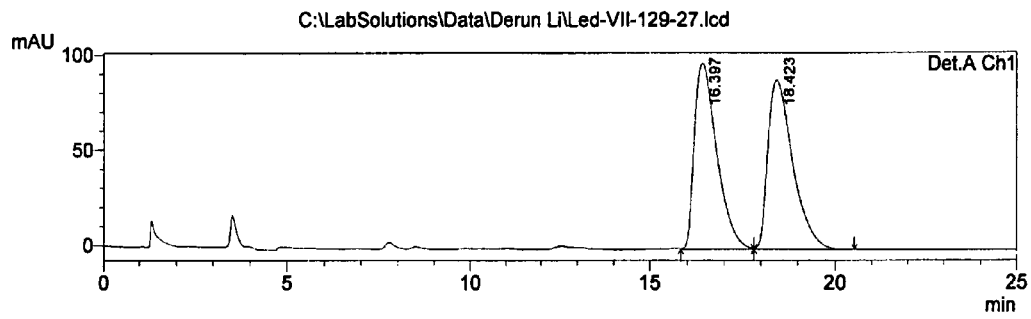
FIG. 17 shows the HPLC analysis for (S)-1,2,3,4-tetrahydronaphthalen-1-ol (Chiralcel OD, 250 mm×4.6 mm, 2% iPrOH in Hexane, 1.0 mL/min, 254 nm).
Figure 17:
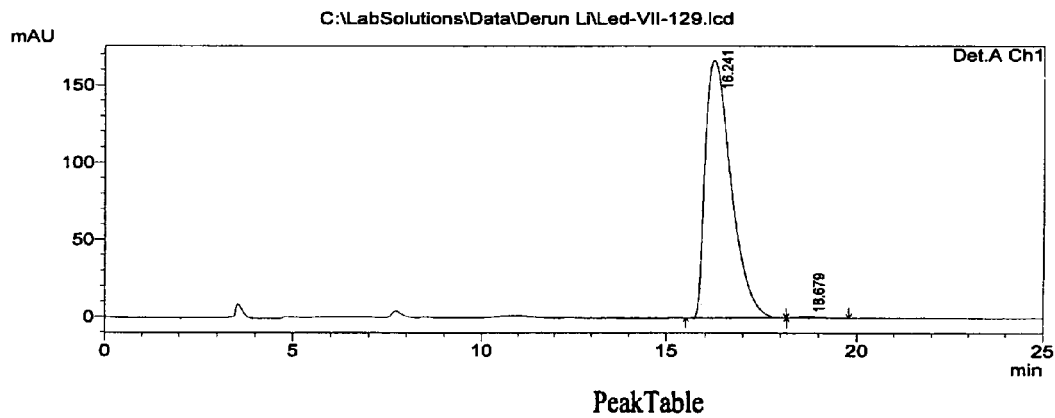

The HPLC analysis for (S)-1,2,3,4-tetrahydronaphthalen-1-ol (Chiralcel OD, 250 mm×4.6 mm, 2% iPrOH in Hexane, 1.0 mL/min, 254 nm) is shown in FIG. 17.

Example 49

(S)-chroman-4-ol

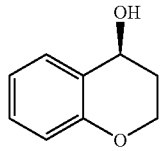

This compound was synthesized in the same manner as Example 39, except chroman-4-one was used instead of acetophenone. 95% yield, 98% ee, HPLC analysis (Chiralcel OJ-H, 250 mm×4.6 mm, 5% iPrOH in Hexane, 1.0 mL/min, 254 nm; $t_r$(major)=16.1 min, $t_r$(minor)=21.2 min); $[\alpha]^{20}{}_D$=-62.0 (c 1.8, CHCl$_3$, lit. (Wettergren 2006) (R)-chroman-4-ol, >99% ee, $[\alpha]^{20}{}_D$=65 (c 1.0, CHCl$_3$)); $^1$H NMR (CDCl$_3$, 300 MHz) δ=7.27 (dd, J=7.5 Hz, 1.5 Hz, 1H), 7.20 (dt, J=9.0 Hz, 1.5 Hz, 1H), 6.90 (dt, J=6.6 Hz, 0.9 Hz, 1H), 6.82 (d, J=8.1 Hz, 1H), 4.70 (q, J=5.1 Hz, 1H), 4.23 (dd, J=3.0 Hz, 1.2 Hz, 1H), 4.21 (d, J=3.9 Hz, 1H), 2.51 (d, J=4.8 Hz, 1H), 2.12-1.91 (m, 2H); $^{13}$C NMR (CDCl$_3$, 75 MHz) δ=154.6, 129.9, 129.8, 124.4, 120.6, 117.1, 63.2, 62.0, 30.9.

Figure 18:
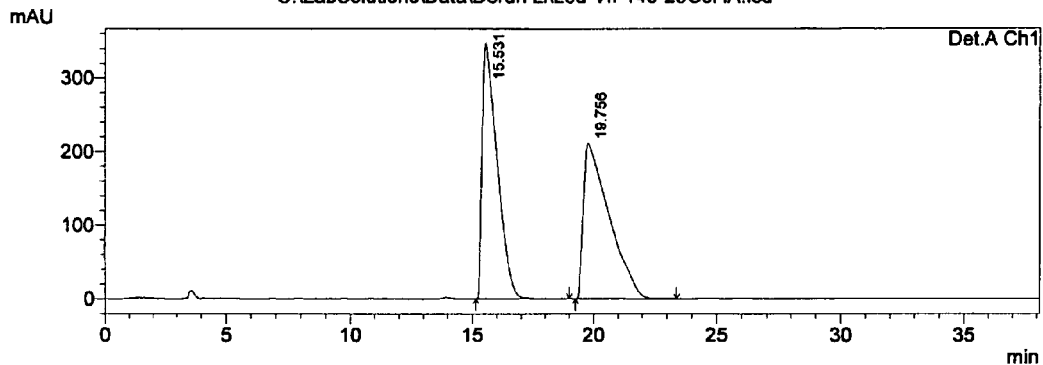
FIG. 18 shows the HPLC analysis for (S)-chroman-4-ol (Chiralcel OJ-H, 250 mm×4.6 mm, 5% iPrOH in Hexane, 1.0 mL/min, 254 nm).
Figure 18:
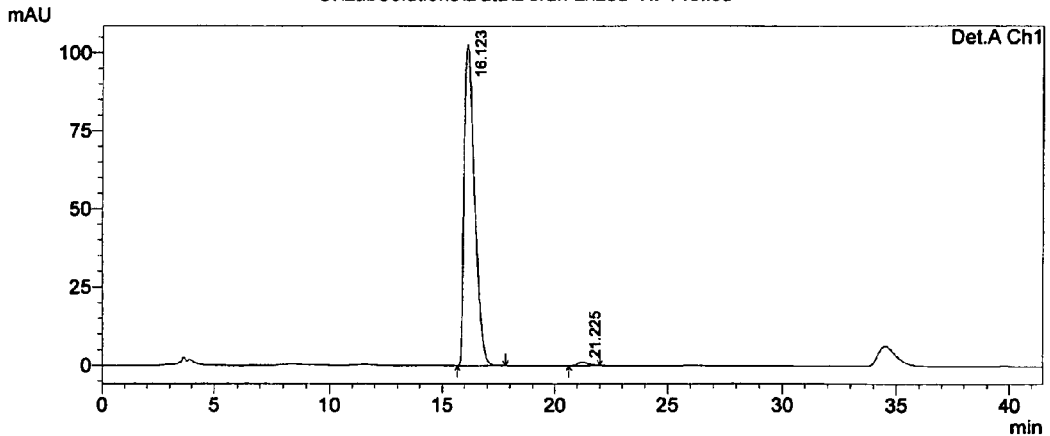

The HPLC analysis for (S)-chroman-4-ol (Chiralcel OJ-H, 250 mm×4.6 mm, 5% iPrOH in Hexane, 1.0 mL/min, 254 nm) is shown in FIG. 18.

Example 50

(S)-1-(naphthalen-2-yl)ethanol

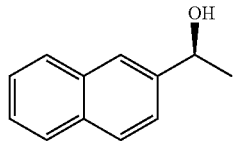

This compound was synthesized in the same manner as Example 39, except 1-(naphthalen-2-yl)ethanone was used instead of acetophenone. 93% yield, 98% ee, HPLC analysis (Chiralcel OJ-H, 250 mm×4.6 mm, 5% iPrOH/Hexane, 1.0 mL/min, 254 nm; $t_r$(major)=25.7 min, $t_r$(minor)=33.7 min); $[\alpha]^{20}{}_D$=-50.0 (c 2.0, CHCl$_3$, lit. (S)-1-(naphthalen-2-yl)ethanol, 94% ee, $[\alpha]^{25}{}_D$=-40.6 (c 0.8, CHCl$_3$)); $^1$H NMR (CDCl$_3$, 300 MHz) δ=7.85-7.79 (m, 2H), 7.52-7.45 (m, 2H), 5.03 (q, J=6.6 Hz, 1H), 2.33 (br s, 1H), 1.57 (d, J=6.3 Hz, 3H); $^{13}$C NMR (CDCl$_3$, 75 MHz) δ=143.3, 133.4, 133.0, 128.4, 128.0, 127.8, 126.2, 125.9, 124.0, 123.9, 70.6, 25.2.

Figure 19:
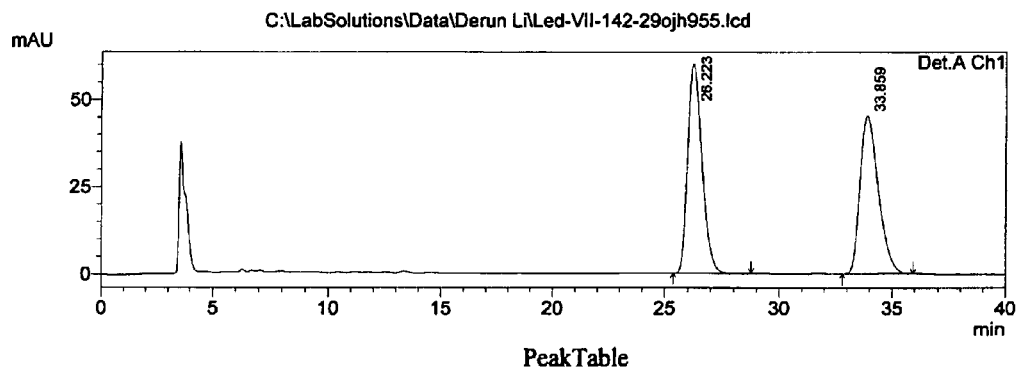
FIG. 19 shows the HPLC analysis for (S)-1-(naphthalen-2-yl)ethanol (Chiralcel OJ-H, 250 mm×4.6 mm, 5% iPrOH/Hexane, 1.0 mL/min, 254 nm).
Figure 19:
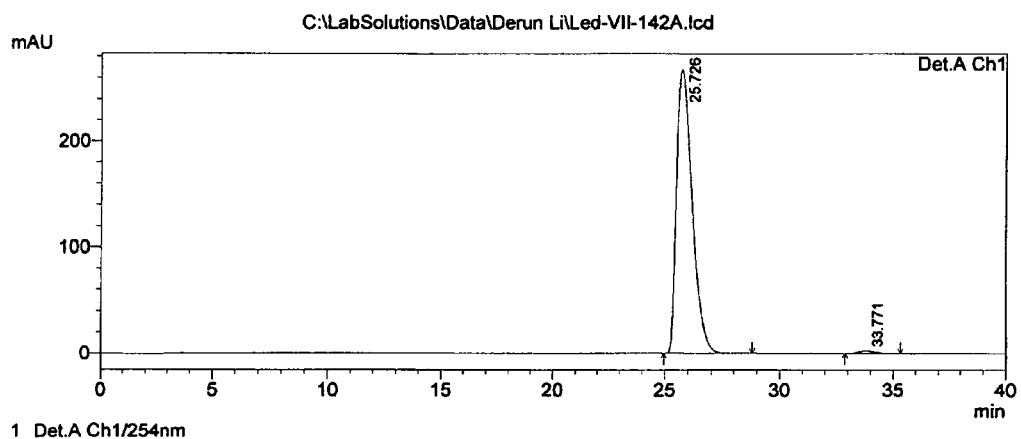

The HPLC analysis for (S)-1-(naphthalen-2-yl)ethanol (Chiralcel OJ-H, 250 mm×4.6 mm, 5% iPrOH/Hexane, 1.0 mL/min, 254 nm) is shown in FIG. 19.

Example 51

(S)-1-(thiophen-2-yl)ethanol

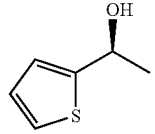

This compound was synthesized in the same manner as Example 39, except the reaction time was 30 hours and 1-(thiophen-2-yl)ethanone was used instead of acetophenone. 66% yield, 97% ee, HPLC analysis (Chiralcel OD, 250 mm×4.6 mm, 2% iPrOH in Hexane, 1.0 mL/min, 254 nm; $t_r$(major)=30.0 min, $t_r$(minor)=38.3 min); $[\alpha]^{20}{}_D$=-24.6 (c 0.90, CHCl$_3$, lit. (Ohkuma 2000) (S)-1-(thiophen-2-yl)ethanol, 99% ee, $[\alpha]^{24}{}_D$=-26.0 (c 1.02, CHCl$_3$)); $^1$H NMR (CDCl$_3$, 300 MHz) δ=7.26-7.21 (m, 1H), 6.98-6.94 (m, 2H), 5.09 (q, J=6.6 Hz, 1H), 2.61 (br s, 1H), 1.57 (d, J=6.3 Hz, 3H); $^{13}$C NMR (CDCl$_3$, 75 MHz) δ=150.0, 126.7, 124.5, 123.3, 66.2, 25.3.

Figure 20:
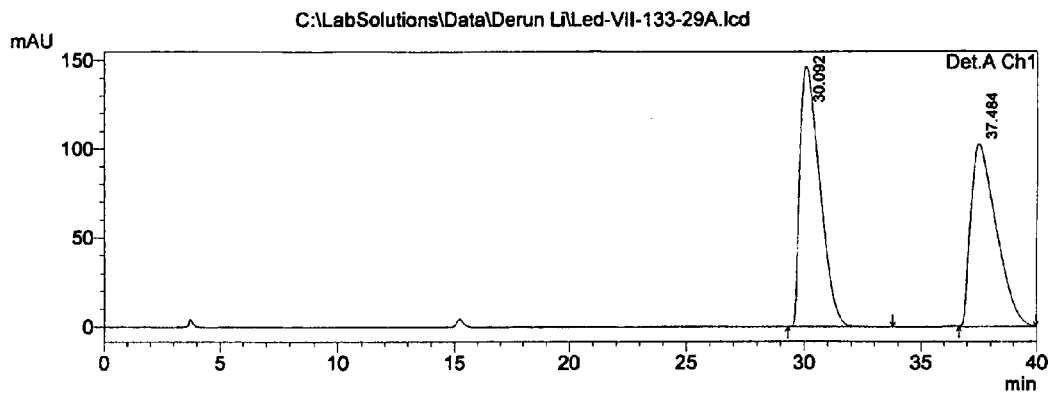
FIG. 20 shows the HPLC analysis for (S)-1-(thiophen-2-yl)ethanol (Chiralcel OD, 250 mm×4.6 mm, 2% iPrOH in Hexane, 1.0 mL/min, 254 nm).
Figure 20:
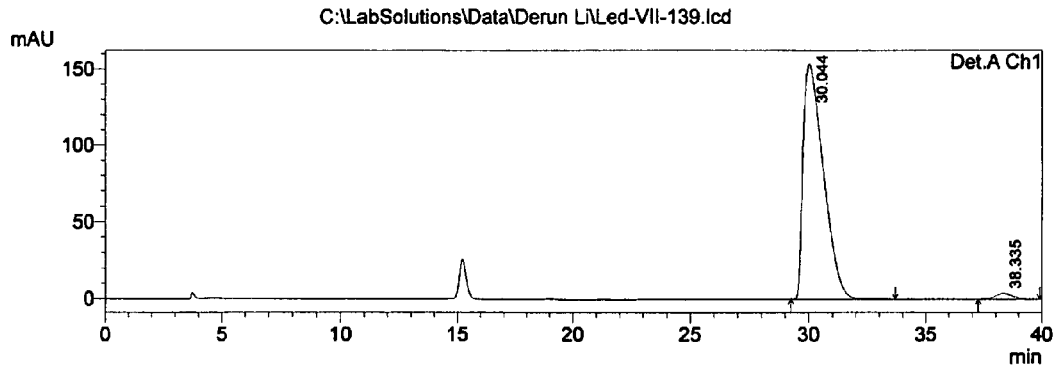

The HPLC analysis for (S)-1-(thiophen-2-yl)ethanol (Chiralcel OD, 250 mm×4.6 mm, 2% iPrOH in Hexane, 1.0 mL/min, 254 nm) is shown in FIG. 20.

Example 52

(S,E)-4-phenylbut-3-en-2-ol

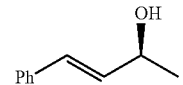

This compound was synthesized in the same manner as Example 39, except (E)-4-phenylbut-3-en-2-one was used instead of acetophenone. 78% yield, 90% ee, HPLC analysis (Chiralcel OD, 250 mm×4.6 mm, 10% iPrOH in Hexane, 0.5 mL/min, 254 nm; $t_r$(major)=22.8 min, $t_r$(minor)=16.0 min);

[α]$^{20}_D$=−28.6 (c 1.4, CHCl$_3$, lit. (Burgess 1991) (S,E)-4-phenylbut-3-en-2-ol, >95% ee, [α]$^{25}_D$=−29.2 (c 2.00, CHCl$_3$)); $^1$H NMR (CDCl$_3$, 300 MHz) δ=7.40-7.22 (m, 5H), 6.57 (d, J=15.9 Hz, 1H), 6.27 (ddd, J=15.9 Hz, 6.3 Hz, 0.9 Hz, 1H), 4.87 (p, J=6.3 Hz, 1H), 2.12 (br s, 1H), 1.37 (d, J=6.3 Hz, 1H); $^{13}$C NMR (CDCl$_3$, 75 MHz) δ=136.8, 133.7, 129.5, 128.7 (2C), 127.7, 126.5 (2C), 69.0, 23.5.

Figure 21:
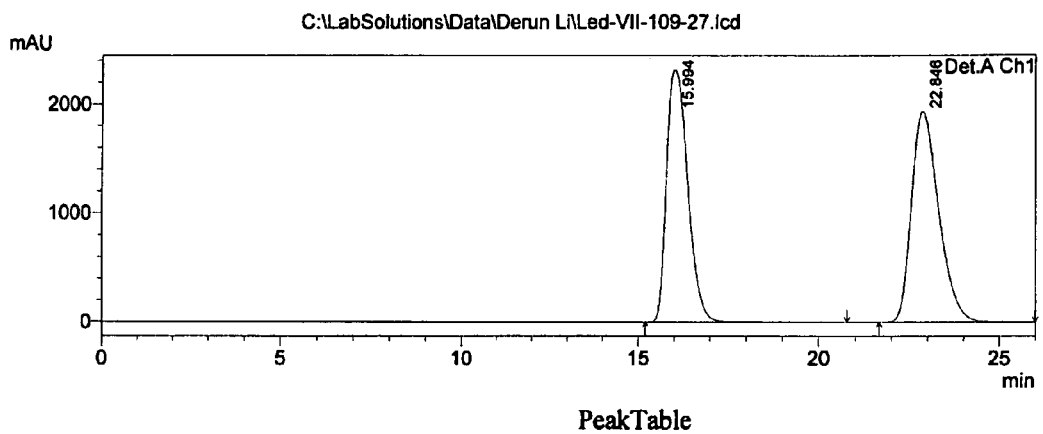
FIG. 21 shows the HPLC analysis for (S,E)-4-phenylbut-3-en-2-ol (Chiralcel OD, 250 mm×4.6 mm, 10% iPrOH in Hexane, 0.5 mL/min, 254 nm).
Figure 21:
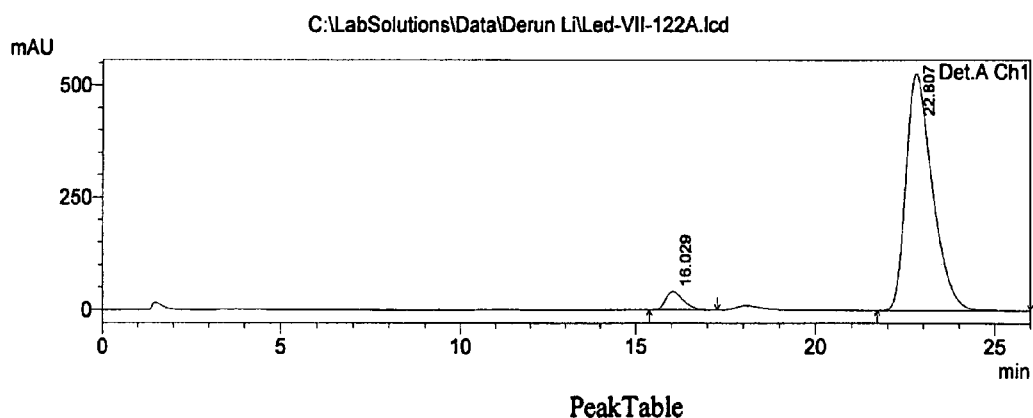

The HPLC analysis for (S,E)-4-phenylbut-3-en-2-ol (Chiralcel OD, 250 mm×4.6 mm, 10% iPrOH in Hexane, 0.5 mL/min, 254 nm) is shown in FIG. 21.

Example 53

(S,E)-6-phenylhex-3-en-2-ol

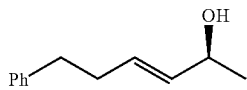

This compound was synthesized in the same manner as Example 39, except (E)-6-phenylhex-3-en-2-one was used instead of acetophenone. 88% yield, 86% ee; HPLC analysis (Chiralcel OD, 250 mm×4.6 mm, 5% iPrOH in Hexane, 1.0 mL/min, 254 nm; t$_r$(major)=20.5 min, t$_r$(minor)=13.0 min); [α]$^{20}_D$=−8.8 (c 1.95, CHCl$_3$); $^1$H NMR (CDCl$_3$, 300 MHz) δ=7.32-7.19 (m, 5H), 5.68 (dt, J=15.6 Hz, 6.5 Hz, 1H), 5.53 (dd, J=15.6 Hz, 6.3 Hz, 1H), 4.26 (p, J=6.3 Hz, 1H), 2.71 (t, J=7.5 Hz, 2H), 2.35 (q, J=7.5 Hz, 2H), 1.68 (br s, 1H), 1.25 (d, J=6.3 Hz, 3H); $^{13}$C NMR (CDCl$_3$, 75 MHz) δ=141.9, 135.0, 130.2, 128.6 (2C), 128.5 (2C), 126.0, 69.1, 35.8, 34.1, 23.5; ES-MS [MH$^+$] m/z 177.1.

Figure 22:
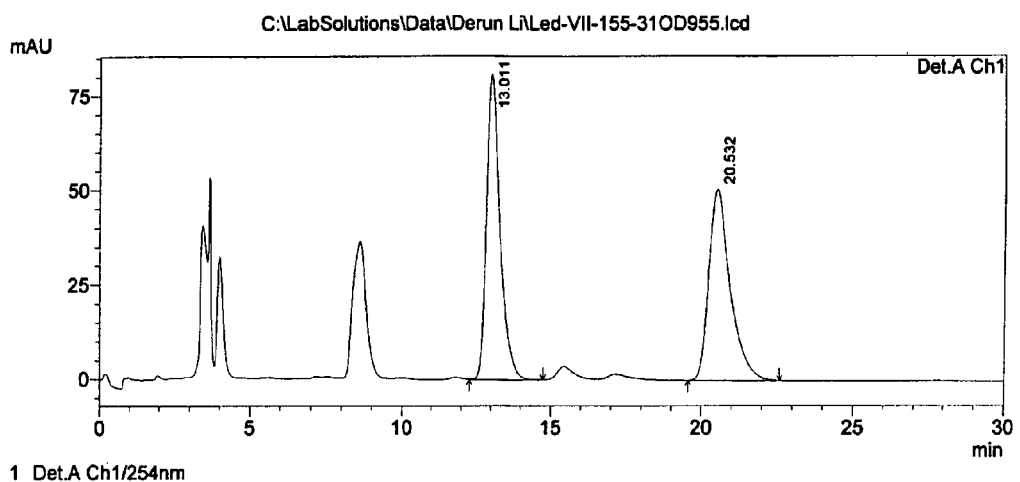
FIG. 22 shows the HPLC analysis for (S,E)-6-phenylhex-3-en-2-ol (Chiralcel OD, 250 mm×4.6 mm, 5% iPrOH in Hexane, 1.0 mL/min, 254 nm).
Figure 22:
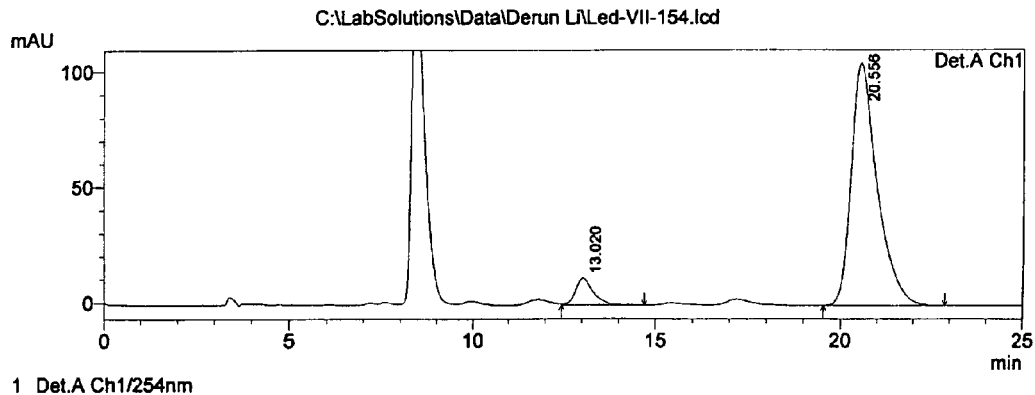

The HPLC analysis for (S,E)-6-phenylhex-3-en-2-ol (Chiralcel OD, 250 mm×4.6 mm, 5% iPrOH in Hexane, 1.0 mL/min, 254 nm) is shown in FIG. 22.

Example 54

(S)-1-cyclohexenylethanol

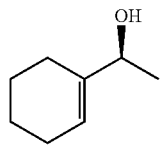

This compound was synthesized in the same manner as Example 39, except 1-cyclohexenylethanone was used instead of acetophenone. 82% yield, 97% ee, HPLC analysis (Chiralcel OB, 250 mm×4.6 mm, 0.5% iPrOH in Hexane, 0.5 mL/min, 202 nm; t$_r$(major)=12.7 min, t$_r$(minor)=16.0 min); [α]$^{20}_D$=−9.5 (c 1.2, CHCl$_3$, lit. (S)-1-cyclohexenylethanol, 91% ee, [α]$^{25}_D$=−9.4 (c 1.5, CHCl$_3$)); $^1$H NMR (CDCl$_3$, 300 MHz) δ=5.67 (br s, 1H), 4.22-4.10 (m, 1H), 2.02-1.99 (m, 4H), 1.67-1.53 (m, 4H), 1.38 (d, J=3.6 Hz, 1H), 1.25 (d, J=6.6 Hz, 3H); $^{13}$C NMR (CDCl$_3$, 75 MHz) δ=141.4, 121.7, 72.4, 25.0, 23.8, 22.8, 22.7, 21.7.

Figure 23:
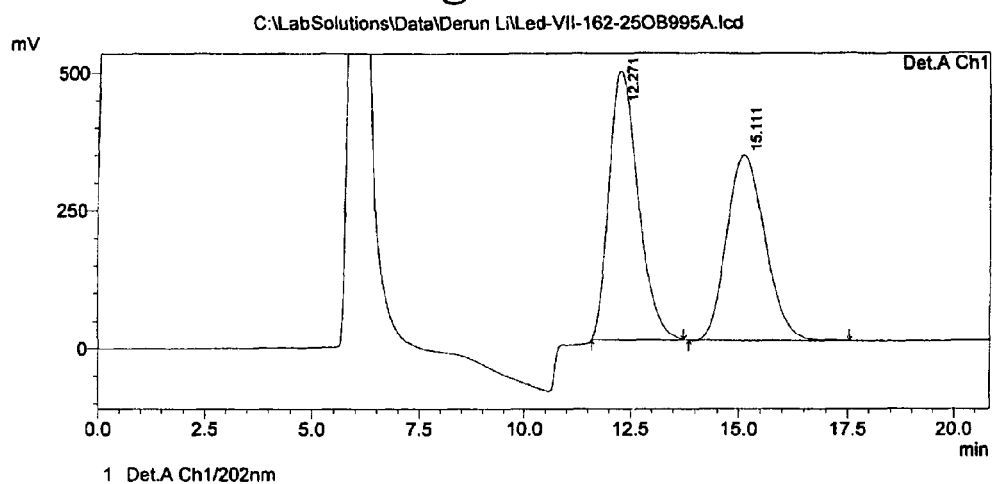
FIG. 23 shows the HPLC analysis for (S)-1-cyclohexenylethanol (Chiralcel OB, 250 mm×4.6 mm, 0.5% iPrOH in Hexane, 0.5 mL/min, 202 nm).
Figure 23:
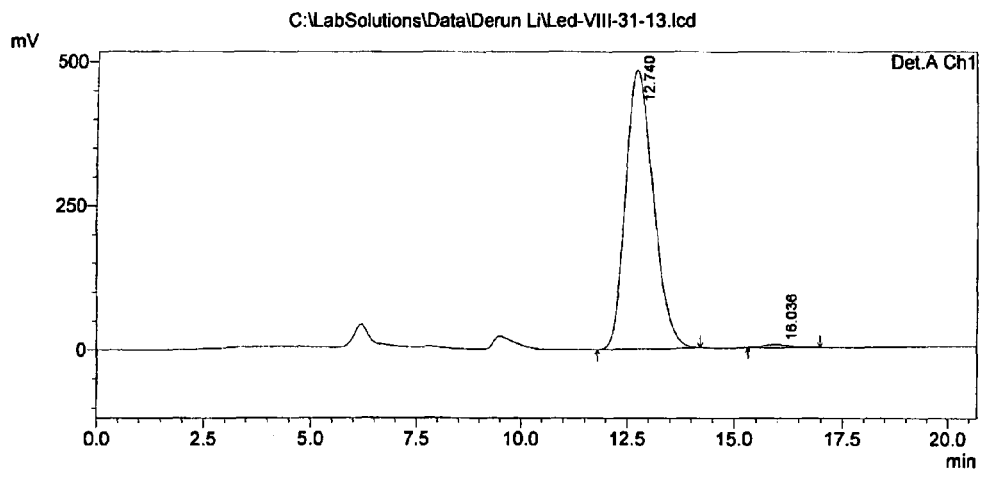

The HPLC analysis for (S)-1-cyclohexenylethanol (Chiralcel OB, 250 mm×4.6 mm, 0.5% iPrOH in Hexane, 0.5 mL/min, 202 nm) is shown in FIG. 23.

Example 55

(S)-4-phenylbutan-2-ol

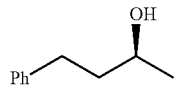

This compound was synthesized in the same manner as Example 39, except thiourea obtained in Example 3 was used instead of the thiourea obtained in Example 1, and 4-phenylbutan-2-one was used instead of acetophenone. 92% yield, 79% ee; HPLC analysis (Chiralcel OD, 250 mm×4.6 mm, 10% iPrOH in Hexane, 0.5 mL/min, 254 nm; t$_r$(major)=15.5 min, t$_r$(minor)=11.1 min); [α]$^{20}_D$=13.8 (c 1.70, CHCl$_3$, lit. (S)-4-phenylbutan-2-ol, 97% ee, [α]$^{22}_D$=18.8 (c 0.86, CHCl$_3$)); $^1$H NMR (CDCl$_3$, 300 MHz) δ=7.34-7.18 (m, 5H), 3.89-3.80 (m, 1H), 2.83-2.64 (m, 2H), 1.89 (br s, 1H), 1.86-1.75 (m, 2H), 1.25 (d, J=6.0 Hz, 3H); $^{13}$C NMR (CDCl$_3$, 75 MHz) δ=142.2, 128.5 (4C), 125.9, 67.5, 40.9, 32.2, 23.6.

Figure 24:
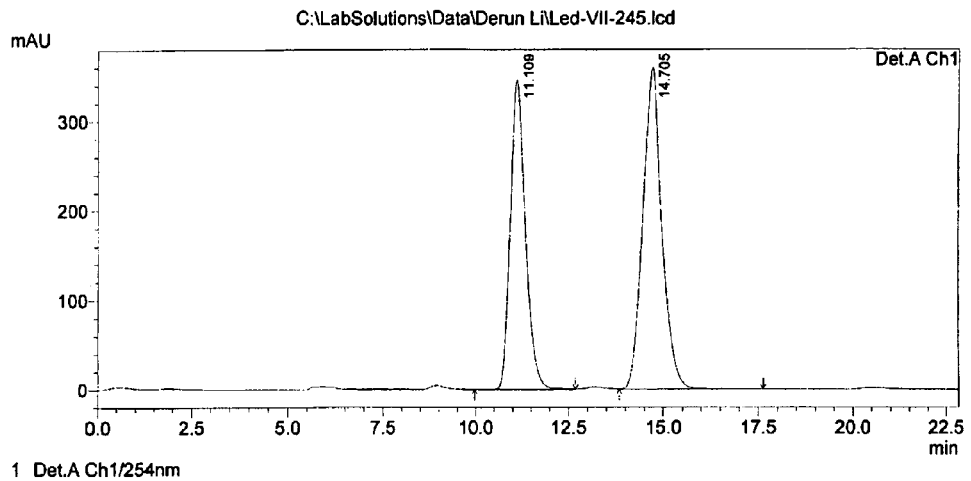
FIG. 24 shows the HPLC analysis for (S)-4-phenylbutan-2-ol (Chiralcel OD, 250 mm×4.6 mm, 10% iPrOH in Hexane, 0.5 mL/min, 254 nm).
Figure 24:
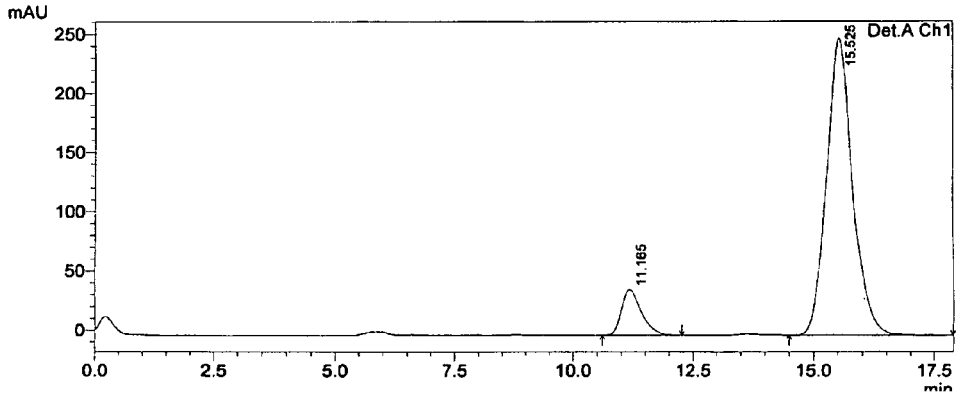

The HPLC analysis for (S)-4-phenylbutan-2-ol (Chiralcel OD, 250 mm×4.6 mm, 10% iPrOH in Hexane, 0.5 mL/min, 254 nm) is shown in FIG. 24.

Example 56

(S)-1-cyclohexylethanol

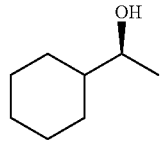

This compound was synthesized in the same manner as Example 39, except thiourea obtained in Example 3 was used instead of thiourea obtained in Example 1, and 1-cyclohexylethanone was used instead of acetophenone. 68% yield, 91% ee; HPLC analysis of 4-nitrobenzoyl ester (Chiralcel OJ-H, 250 mm×4.6 mm, 0.1% iPrOH in Hexane, 0.4 mL/min, 254 nm; t$_r$(major)=31.9 min, t$_r$(minor)=35.0 min); [α]$^{20}_D$=3.71 (c 0.70, CHCl$_3$, lit. (Gamble 1998) (R)-1-cyclohexylethanol, 67% ee, [α]$_D$=−1.90 (c 0.75, CHCl$_3$)); $^1$H NMR (CDCl$_3$, 300 MHz) δ=3.52 (p, J=6.3 Hz, 1H), 1.85-1.63 (m, 5H), 1.52 (br s, 1H), 1.35-0.85 (m, 6H), 1.13 (d, J=6.3 Hz, 3H); $^{13}$C NMR (CDCl$_3$, 75 MHz) δ=72.3, 45.2, 28.8, 28.5, 26.6, 26.3, 26.2, 20.5.

Figure 25:
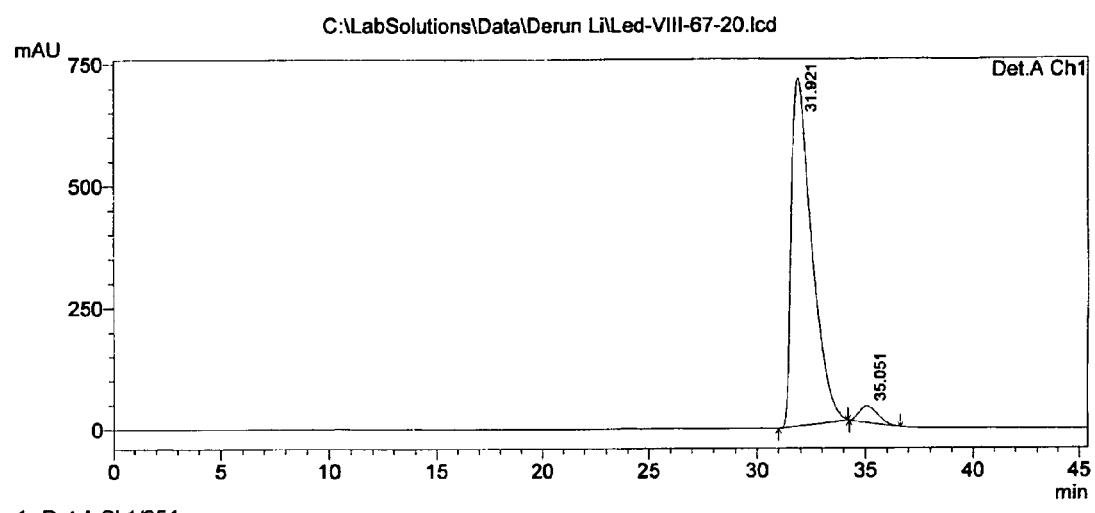
FIG. 25 shows the HPLC analysis for (S)-1-cyclohexylethyl 4-nitrobenzoate (Chiralcel OJ-H, 250 mm×4.6 mm, 0.1% iPrOH in Hexane, 0.4 mL/min, 254 nm).

The HPLC analysis for (S)-1-cyclohexylethyl 4-nitrobenzoate (Chiralcel OJ-H, 250 mm×4.6 mm, 0.1% iPrOH in Hexane, 0.4 mL/min, 254 nm) is shown in FIG. 25.

REFERENCES CITED

Other Publications

Burgess, K.; Jennings, L. D. *J. Am. Chem. Soc.* 1991, 113, 6129-6139.

Carter, M. B.; Schiøtt, B.; Gutiérrez, A.; Buchwald, S. L. *J. Am. Chem. Soc.* 1994, 116, 11667.

Corey, E. J.; Helal, C. J. *Angew. Chem. Int. Ed.* 1998, 37, 1986-2012.
Gamble, M. P.; Smith, A. R. C.; Wills, M. *J. Org. Chem.* 1998, 63, 6068-6071.
Huang, X.; Ortiz-Marciales, M.; Huang, K.; Stepanenko, V.; Merced, F. G.; Ayala, A. M.; Correa, W.; Jesu'S, M. *J. Org. Lett.* 2007, 9, 1793-1795.
*J. Am. Chem. Soc.* 2005, 127, 8964-8965.
*J. Am. Chem. Soc.* 2007, 129, 15872-15883.
Lutz, C.; Knochel, P. *J. Org. Chem.* 1997, 62, 7895-7898.
Node, M.; Nishide, K.; Shigeta, Y.; Shiraki, H.; Obata, K. *J. Am. Chem. Soc.* 2000, 122, 1927-1936.
Ohkuma, T.; Koizumi, M.; Yoshida, M.; Noyori, R. *Org. Lett.* 2000, 2, 1749-1751.
Sokeirik, Y. S.; Mori, H.; Omote, M.; Sato, K.; Tarui, A.; Kumadaki, I.; Ando, A. *Org. Lett.* 2007, 9, 1927-1929.
Tanaka, K.; Katsurada, M.; Ohno, F.; Shiga, Y.; Oda, M.; Miyagi, M.; Takehara, J.; Okano, K. *J. Org. Chem.* 2000, 65, 432.
Utsukihara, T.; Misumi, O.; Kato, N.; Kuroiwa, T.; Horiuchi C. A. *Tetrahedron: Asymmetry* 2006, 17, 1179-1185.
Wettergren, J.; Bogevig, A.; Portier, M.; Adolfssona, H. *Adv. Synth. Catal.* 2006, 348, 1277-1282.

What is claimed is:

1. A chiral thiourea represented by formula (II):

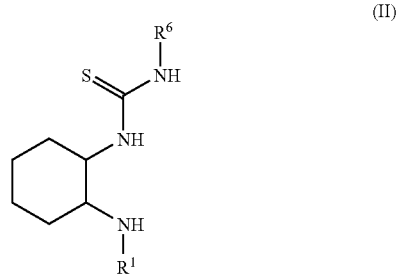

wherein $R^1$ is a substituted or un-substituted aralkyl group or a substituted or un-substituted aryl group;
$R^6$ is a substituted or un-substituted lower alkyl group, a substituted or un-substituted aralkyl group, a substituted or un-substituted aryl group, a substituted or un-substituted heteroaryl group, or is:

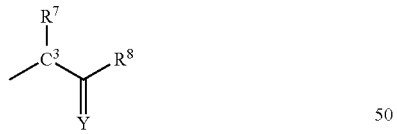

wherein $C^3$ is a chiral carbon atom, Y is S or O, and $R^7$ and $R^8$ independently are an alkyl, alkenyl, alkynyl, acyl, thioacyl, alkylthio, imine, amide, phosphoryl, phosphonate, phosphine, carbonyl, carboxyl, carboxamide, anhydride, silyl, thioakyl, alkylsulfonyl, arylsulfonyl, ketones, aldehyde, ester, heteroalkyl, amidine, acetal, ketal, aryl, heteroaryl, aziridine, carbamate, imide, oxime, sulfonamide, thioamide, thiocarbamate, urea, or thiourea.

2. A method to enantioselectively reduce a prochiral ketone to a secondary chiral alcohol, comprising:
reacting the prochiral ketone with the chiral thiourea of claim 1 in the presence of a borane and a solvent.

3. The method of claim 2, wherein the borane is $BH_3.THF$, $BH_3.Me_2S$, $BH_3.1,4$-thioxane, $BH_3$.diethylaniline, or catecholborane.

4. The method of claim 2, wherein the prochiral ketone is represented by:

wherein $R^{11}$ and $R^{12}$ are inert to borane.

5. The method of claim 4, wherein $R^{11}$ and $R^{12}$ are alkyl, aryl, or aralkyl organic radicals.

6. The method of claim 4, wherein $R^{11}$ and $R^{12}$ are independently substituted with alkyl, alkoxy, or halo substituents.

7. The method of claim 2, wherein the prochiral ketone is cyclic.

8. The method of claim 2, wherein the solvent is an aprotic, non-basic solvent.

9. The method of claim 8, wherein the solvent is aromatic hydrocarbons, ethers, aliphatic hydrocarbons, or halogenated hydrocarbons.

10. The method of claim 8, wherein the solvent is benzene, toluene, tetrahydrofuran, tetrahydropyran, or diethyl ether.

11. The method of claim 2, wherein the prochiral ketone and the chiral thiourea are dissolved in the solvent.

12. The method of claim 2, wherein the chiral thiourea is present at an amount that is sub-stoichiometric with respect to the prochiral ketone.

13. The method of claim 2, wherein the ratio of chiral thiourea to prochiral ketone is less than about 0.1 moles of chiral thiourea to about 1 mole of prochiral ketone.

14. The method of claim 2, wherein the ratio of the borane to prochiral ketone is about 1 mole to about 10 moles of the borane to about 1 mole of prochiral ketone.

15. The method of claim 2, wherein the reacting step produces a reactive mixture.

16. The method of claim 15, further comprising the steps of quenching the reactive mixture with an alcohol, treating the reactive mixture with a base, and isolating the secondary chiral alcohol.

17. A compound selected from the group consisting of:
A. 1-((1R,2R)-2-(benzylamino)cyclohexyl)-3-(3,5-bis(trifluoromethyl)phenyl)thiourea:

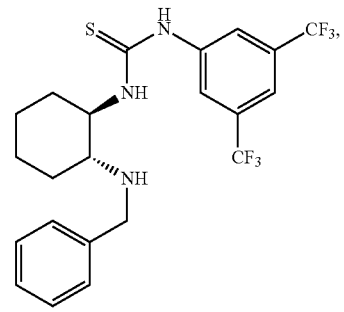

B. (S)-2-(3-((1R,2R)-2-(benzylamino)cyclohexyl)thioureido)-N,3,3-trimethylbutanamide:

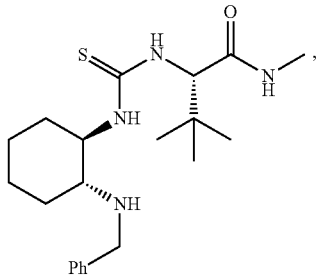

C. (S)—N-benzyl-2-(3-((1R,2R)-2-(benzylamino)cyclohexyl)thioureido)-N,3,3-trimethylbutanamide:

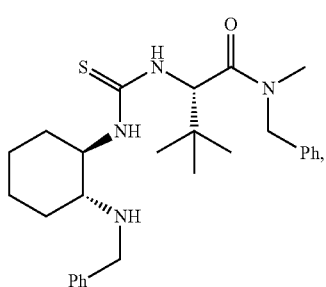

D. (S)-2-(3-((1R,2R)-2-(benzylamino)cyclohexyl)thioureido)-N—((R)-1-(dimethylamino)-3-methyl-1-oxobutan-2-yl)-3,3-dimethylbutanamide:

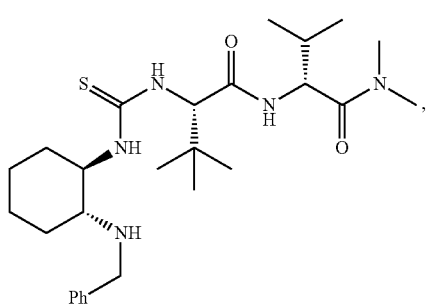

E. 1-(3,5-bis(trifluoromethyl)phenyl)-3-((1R,2R)-2-(4-methoxybenzylamino)cyclohexyl)thiourea:

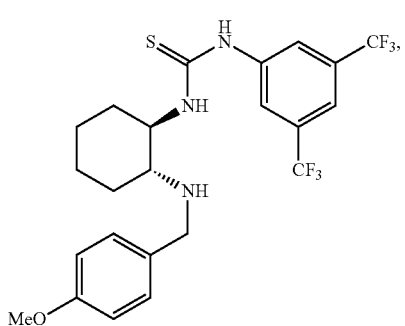

F. 1-(3,5-bis(trifluoromethyl)phenyl)-3-((1R,2R)-2-(4-nitrobenzylamino)cyclohexyl)thiourea:

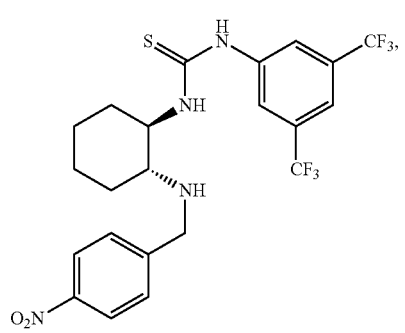

G. 1-(3,5-bis(trifluoromethyl)phenyl)-3-((1R,2R)-2-(naphthalen-1-ylmethylamino)cyclohexyl)thiourea:

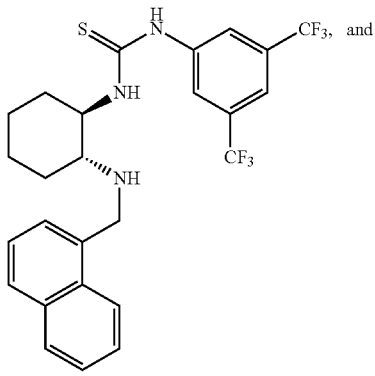

H. 1-(3,5-bis(trifluoromethyl)phenyl)-3-((1R,2R)-2-(naphthalen-2-ylmethylamino)cyclohexyl)thiourea:

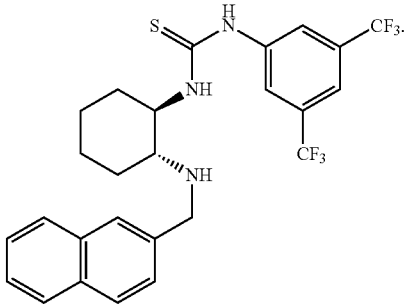

18. A compound selected from the group consisting of:

A. 1-(3,5-bis(trifluoromethyl)phenyl)-3-((1R,2R)-2-(2-bromobenzylamino)cyclohexyl)thiourea:

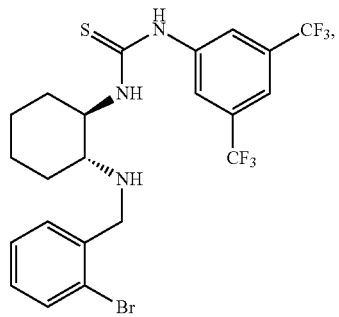

B. 1-(3,5-bis(trifluoromethyl)phenyl)-3-((1R,2R)-2-(2,4-dimethoxybenzylamino)cyclohexyl)thiourea:

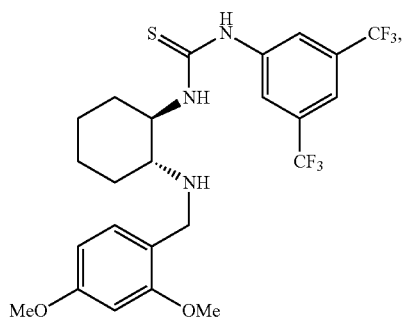

C. 1-((1R,2R)-2-(benzylamino)cyclohexyl)-3-phenylthiourea:

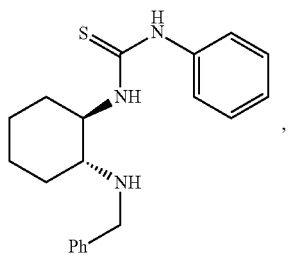

D. 1-((1R,2R)-2-(benzylamino)cyclohexyl)-3-(perfluorophenyl)thiourea:

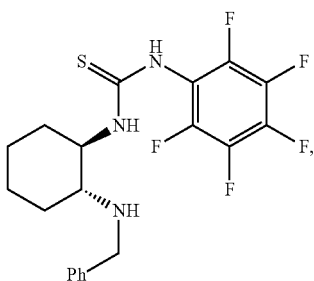

E. 1-((1R,2R)-2-(benzylamino)cyclohexyl)-3-(4-methoxyphenyl)thiourea:

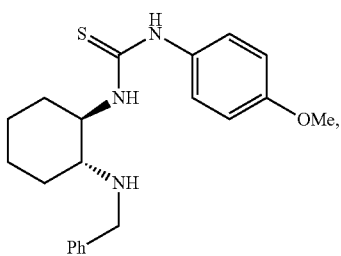

F. 1-((1R,2R)-2-(benzylamino)cyclohexyl)-3-(4-nitrophenyl)thiourea:

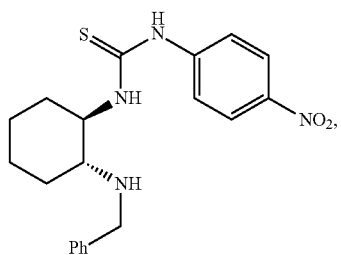

G. 1-((1R,2R)-2-(benzylamino)cyclohexyl)-3-cyclohexylthiourea:

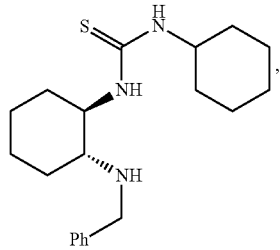

H. 1-((1R,2R)-2-(benzylamino)cyclohexyl)-3-methylthiourea:

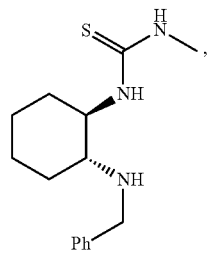

I. 1-((1R,2R)-2-(benzylamino)cyclohexyl)-3-((R)-1-(naphthalen-1-yl)ethyl)thiourea:

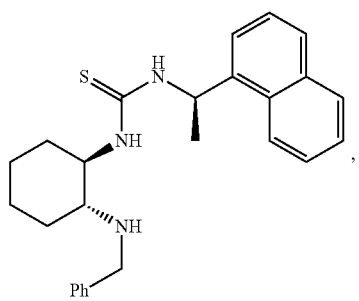

J. 1-((1R,2R)-2-(benzylamino)cyclohexyl)-3-((S)-1-(naphthalen-1-yl)ethyl)thiourea;

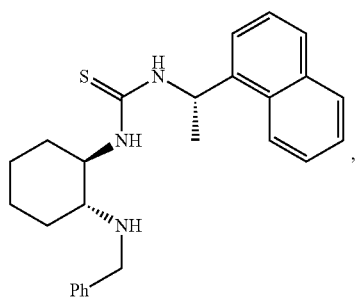

K. (S)-2-(3-((1S,2S)-2-(benzylamino)cyclohexyl)thioureido)-N,3,3-trimethylbutanamide:

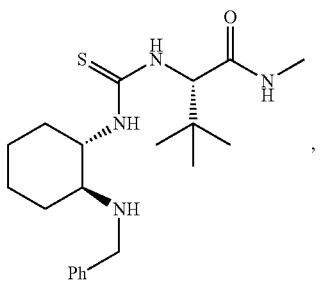

L. (S)-2-(3-((1R,2R)-2-(benzylamino)cyclohexyl)thioureido)-N-tert-butyl-3,3-dimethylbutanamide:

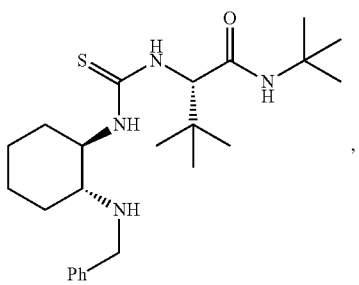

M. (S)-2-(3-((1S,2S)-2-(benzylamino)cyclohexyl)thioureido)-N-tert-butyl-3,3-dimethylbutanamide:

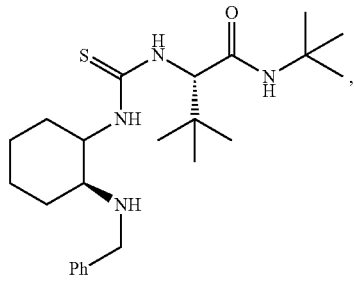

N. (S)—N-benzyl-2-(3-((1S,2S)-2-(benzylamino)cyclohexyl)thioureido)-N,3,3-trimethylbutanamide:

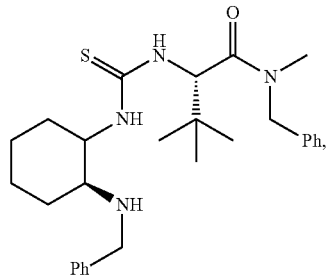

O. 1-((1R,2R)-2-(benzylamino)cyclohexyl)-3-((1R,2R,3R,5S)-2,6,6-trimethylbicyclo[3.1.1]heptan-3-yl)thiourea:

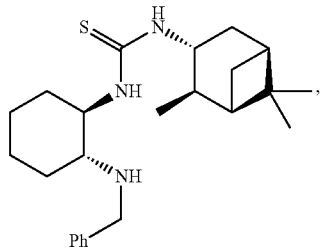

P. 1-((1S,2S)-2-(benzylamino)cyclohexyl)-3-((1R,2R,3R,5S)-2,6,6-trimethylbicyclo[3.1.1]heptan-3-yl)thiourea:

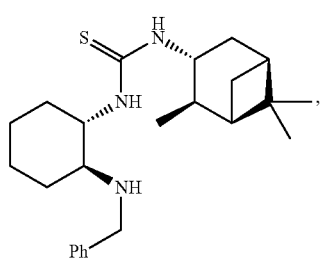

Q. (S)-2-(3-((1S,2S)-2-(benzylamino)cyclohexyl)thioureido)-N—((R)-1-(dimethylamino)-3-methyl-1-oxobutan-2-yl)-3,3-dimethylbutanamide:

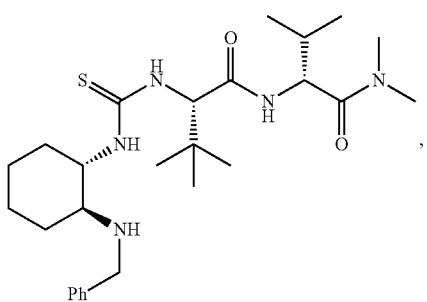

R. (S)-2-(3-((1R,2R)-2-(benzylamino)cyclohexyl)thioureido)-N—((S)-1-(dimethylamino)-3-methyl-1-oxobutan-2-yl)-3,3-dimethylbutanamide:

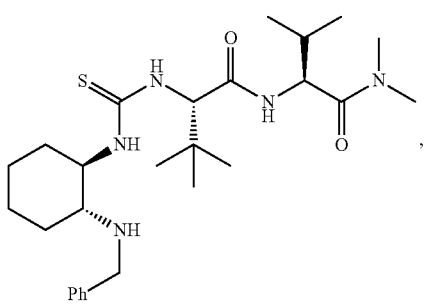

S. (S)-2-(3-((1S,2S)-2-(benzylamino)cyclohexyl)thioureido)-N—((S)-1-(dimethylamino)-3-methyl-1-oxobutan-2-yl)-3,3-dimethylbutanamide:

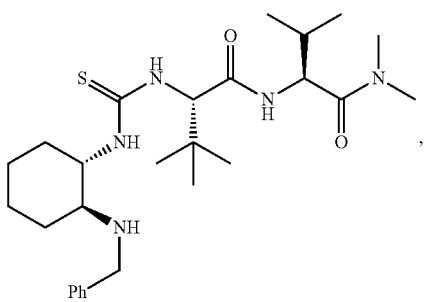

T. 1-((1R,2R)-2-(benzylamino)cyclohexyl)-3-((S)-3,3-dimethyl-1-oxo-1-(piperidin-1-yl)butan-2-yl)thiourea:

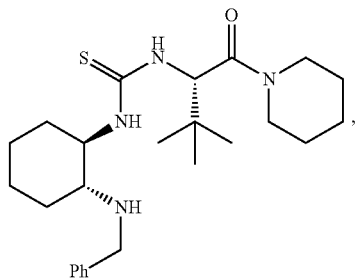

U. 1-((1S,2S)-2-(benzylamino)cyclohexyl)-3-((S)-3,3-dimethyl-1-oxo-1-(piperidin-1-yl)butan-2-yl)thiourea:

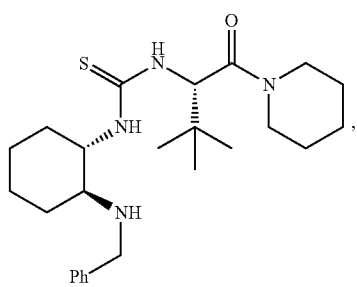

V. (S)—N-benzyl-2-(3-((1R,2R)-2-(benzylamino)cyclohexyl)thioureido)-N-methylpropanamide:

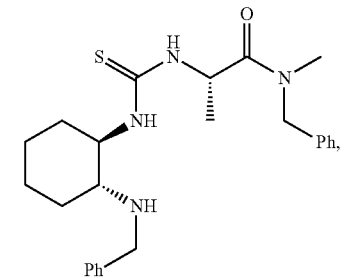

W. (S)—N-benzyl-2-(3-((1S,2S)-2-(benzylamino)cyclohexyl)thioureido)-N-methylpropanamide:

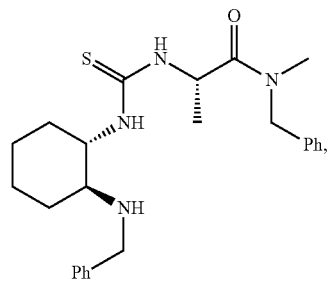

X. (S)—N,N-dibenzyl-2-(3-((1R,2R)-2-(benzylamino)cyclohexyl)thioureido)-3,3-dimethylbutanamide:

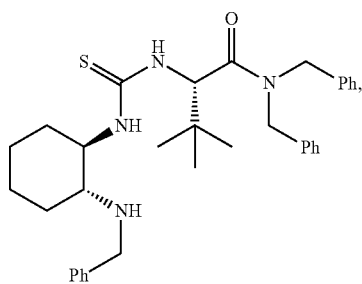

Y. (S)—N,N-dibenzyl-2-(3-((1S,2S)-2-(benzylamino)cyclohexyl)thioureido)-3,3-dimethylbutanamide:

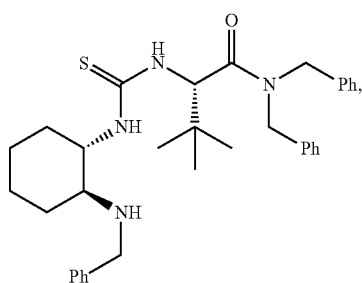

Z. (S)—N-benzyl-2-(3-((1R,2R)-2-(benzylamino)cyclohexyl)thioureido)-N,4-dimethylpentanamide:

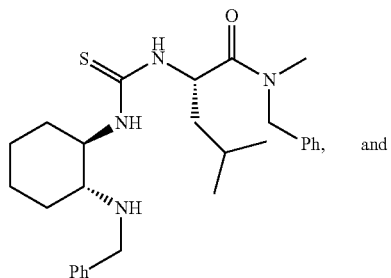

and

AA. (S)—N-benzyl-2-(3-((1S,2S)-2-(benzylamino)cyclo-hexyl)thioureido)-N,4-dimethylpentanamide:
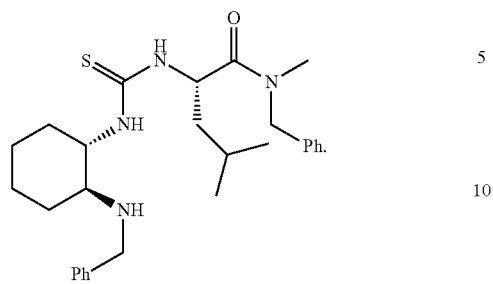
* * * * *